(12) United States Patent
Fan et al.

(10) Patent No.: US 7,622,265 B2
(45) Date of Patent: Nov. 24, 2009

(54) METHODS AND COMPOSITIONS FOR MODULATING PROSTASIN

(75) Inventors: Bin Fan, San Mateo, CA (US); Daniel K. Kirchhofer, Los Altos, CA (US)

(73) Assignee: Genentech, Inc., South San Francisco, CA (US)

( * ) Notice: Subject to any disclaimer, the term of this patent is extended or adjusted under 35 U.S.C. 154(b) by 398 days.

(21) Appl. No.: 11/359,865

(22) Filed: Feb. 22, 2006

(65) Prior Publication Data

US 2006/0210570 A1 Sep. 21, 2006

Related U.S. Application Data

(60) Provisional application No. 60/654,918, filed on Feb. 22, 2005.

(51) Int. Cl.
*G01N 33/53* (2006.01)
(52) U.S. Cl. ...................................................... 435/7.1
(58) Field of Classification Search ........................ None
See application file for complete search history.

(56) References Cited

OTHER PUBLICATIONS

Adachi et al., "Activation of Epithelial Sodium Channels by Prostasin in Xenopus Oocytes" *J Am Soc Nephrol* 12(6):1114-1121 (2001).
Benaud et al., "Regulation of the activity of matriptase on epithelial cell surfaces by a blood-derived factor" *Eur J Biochem* 268(5):1439-1447 (2001).
Bouton et al., "The Serpin Protease-Nexin 1 is Present in Rat Aortic Smooth Muscle Cells and is Upregulated in L-NAME Hypertensive Rats" *Arterioscler Thromb Vasc Biol* 23(1):142-147 (Jan. 2003).
Chen et al., "Down-Regulation of Prostasin Serine Protease: A Potential Invasion Suppressor in Prostate Cancer"*Prostate* 48 (2) :93-103 (Jun. 15, 2001).
Chen et al., "Prostasin is a Glycosylphosphatidylinositol-anchored Active Serine Protease" *J Biol Chem* 276(24):21434-21442 (2001).
Chen et al., "Prostasin Serine Inhibits Breast Cancer Invasiveness and is Transcriptionally Regulated by Promoter DNA Methylation" *Int. J Cancer* 97(3):323-329 (2002).
Chen et al., "Regulation of Prostasin Expression and Function in the Prostate" *Prostate* 59(1):1-12 (2004).
Denda et al., "Functional characterization of Kunitz domains in hepatocyte growth factor activator inhibitor type 1" *J Biol Chem.* 277(16):14053-14059 (Apr. 19, 2002).
Dennis et al., "Potent and selective Kunitz domain inhibitors of plasma kallikrein designed by phage display" *J Biol Chem.* 270(43):25411-25417 (Oct. 27, 1995).
Donaldson et al., "Regulation of the Epithelial Sodium Channel by Serine Proteases in Human Airways" *J Biol Chem* 277(10):8338-8345 (2002).
Fan et al., "Identification of hepatocyte growth factor activator inhibitor-1B as a potential physiological inhibitor of prostasin Identification of hepatocyte growth factor activator inhibitor-1B as a potential physiological inhibitor of prostasin" *J Biol Chem.* 280(41):34513-34520 (Oct. 14, 2005).

Graeber and Eisenberg, "Bioinformatic Identification of Potential Autocrine Signaling Loops in Cancers from Gene Expression Profiles" *Nat. Genet.* 29(3):295-300 (Nov. 2001).
Itoh et al., "Genomic Structure and Chromosomal Localization of the Human Hepatocyte Growth Factor Activator Inhibitor Type 1 and 2 Genes" *Eur J Biochem* 267(11):3351-3359 (2000).
Itoh.et al., "Upregulation of HGF Activator Inhibitor Type 1 but not Type 2 along with Regeneration of Intestinal Mucosa" *Am J Physiol Gastrointest Liver Physiol.* 278(4):G635-G643 (2000).
Kataoka et al., "Activation of Hepatocyte Growth Factor/Scatter Factor in Colorectal Carcinoma" *Cancer Research* 60:6148-6159 (Nov. 1, 2000).
Kataoka et al., "Distribution of hepatocyte growth factor activator inhibitor type.1 (HAI-1) in human tissues: Cellular surface localization of HAI-1 in simple columnar epithelium and its modulated expression in injured and regenerative tissues" *J Histochem Cytochem.* 47(5):673-682 (May 1999).
Kataoka et al., "Evaluation of hepatocyte growth factor activator inhibitor expression in normal and malignant colonic mucosa" *Cancer Lett.* 128(2):219-227 (Jun. 19, 1998).
Kataoka et al., "Hepatocyte growth factor activator inhibitor type 1 is a specific cell surface binding protein of hepatocyte growth factor activator (HGFA) and regulates HGFA activity in the pericellular microenvironment" *J Biol Chem* 275 (51) :40453-40462 (2000).
Kataoka et al., "Roles of Hepatocyte Growth Factor (HGF) Activator and HGF Activator Inhibitor in the Pericellular Activation of HGF/Scatter Factor" *Cancer Metastasis Rev* 22(2) :223-236 (2003).
Kawaguchi et al., "Purification and cloning of hepatocyte growth factor activator inhibitor type 2, a Kunitz-type serine protease inhibitor" *J Biol Chem.* 272(44):27558-27564 (Oct. 31, 1997).
Kirchhofer et al., "Tissue expression, protease specificity, and Kunitz domain functions of hepatocyte growth factor activator inhibitor-1B (HAI-1B), a new splice variant of HAI-1" *J Biol Chem.* 278(38):36341-36349 (Sep. 19, 2003).
Kohler et al., "Continuous cultures of fused cells secreting antibody of predefined specificity" *Nature* 256:495 (Aug. 7, 1975).
Lee et al., "Activation of Hepatocyte Growth Factor and Urokinase/Plasmingoen Activator by Matriptase, an Epithelial Membrane Serine Protease" *Journal of Biological Chemistry* 275:36720-36725 (2000).
Lin et al., "Characterization of a Novel, Membrane-Bound, 80-kDa Matrix-Degrading Protease from Human Breast Cancer Cells. Monoclonal Antibody Production, Isolation, and Localization" *J Biol Chem* 272(14):9147-9152 (Apr. 4, 1997).
Lin et al., "Purification and characterization of a complex containing matriptase and a kunitz-type serine protease inhibitor from human milk" *J Biol Chem* 274(26):18237-18242 (Jun. 25, 1999).
Liu et al., "NetAffx: Affymetrix Probesets and Annotations" *Nucleic Acids Res* 31(1):82-86 (2003).
Marlor et al., "Identification and cloning of human placental bikunin, a novel serine protease inhibitor containing two Kunitz domains" *J Biol Chem.* 272(18):12202-12208 (May 2, 1997).
Mok et al., "Prostasin, a Potential Serum Marker for Ovarian Cancer: Identification Through Microarray Technology" *J Natl Cancer Inst.* 93(19):1458-1464 (Oct. 31, 2001).
Muthukumar et al., "Serine Proteinase Inhibitor-9, an Endogenous Blocker of Granzyme B/Perforin Lytic Pathway, is Hyperexpressed during Acute Rejection of Renal Allografts" *Transplantation* 75(9):1565-1570 (2003).

(Continued)

*Primary Examiner*—Christopher H Yaen
(74) *Attorney, Agent, or Firm*—Cara Coburn

(57) ABSTRACT

The invention provides methods and compositions related to modulating prostasin.

11 Claims, 6 Drawing Sheets

OTHER PUBLICATIONS

Oberst et al., "Expression of the serine protease matriptase and its inhibitor HAI-1 in epithelial ovarian cancer: correlation with clinical outcome and tumor clinicopathological parameters" *Clin Cancer Res.* 8(4):1101-1107 (Apr. 2002).

Parr et al., "Expression of hepatocyte growth factor/scatter factor, its activator, inhibitors and the c-Met receptor in human cancer cells" *Int J Oncol.* 19(4):857-863 (Oct. 2001).

Phillips et al., "A role for the Granzyme B Inhibitor Serine Protease Inhibitor 6 in CD8+ Memory Cell Homeostasis" *J Immunol.* 173(6):3801-3809 (2004).

Richard et al., "Protease Nexin-1: A Cellular Serpin Down-Regulated by Thrombin in Rat Aortic Smooth Muscle Cells" *J Cell Physiol.* 201(1):138-145 (2004).

Shimomura et al., "Hepatocyte Growth Factor Activator Inhibitor, a Novel Kunitz-type Serine Protease Inhibitor" *Journal of Biological Chemistry* 272(10):6370-6376 (Mar. 7, 1997).

Shimomura, T. et al., "Multiple Sites of Proteolytic Cleavage to Release Soluble Forms of Hepatocyte Growth Factor Activator Inhibitor Type 1 from a Transmembrane Form" *J Biochem (Tokyo)* 126(5):821-828 (1999).

Shipway, A. et al., "Biochemical Characterization of Prostasin, a Channel Activating Protease" *Biochem Biophys Res Commun.* 324(2):953-963 (2004).

Takahashi, S. et al., "Down-Regulated Expression of Prostasin in High-Grade or Hormone-Refractory Human Prostate Cancers" *Prostate* 54(3):187-193 (2003).

Tong, Z. et al., "Prostasin, a Membrane-Anchored Serine Peptidase, Regulates Sodium Currents in JME/CF15 Cells, a Cystic Fibrosis Airway Epithelial Cell Line" *Am J Physiol Lung Cell Mol Physiol.* 287:L928-L935 (Nov. 2004).

Tyagi et al., "Co-Expression of Tissue Inhibitor and Matrix Metalloproteinase in Myocardium" *J Mol Cell Cardiol.* 27(10):2177-2189 (1995).

Yu et al., "Molecular Cloning, Tissue-specific Expression, and Cellular Localization of Human Prostasin mRNA" *J Biol Chem.* 270(22):13483-13489 (Jun. 2, 1995).

Yu et al., "Prostasin is a Novel Human Serine Protenaise from Seminal Fluid Purification, Tissue Distribution, and Localization in Prostate Gland" *J Biol Chem.* 269(29):18843-18848 (Jul. 22, 1994).

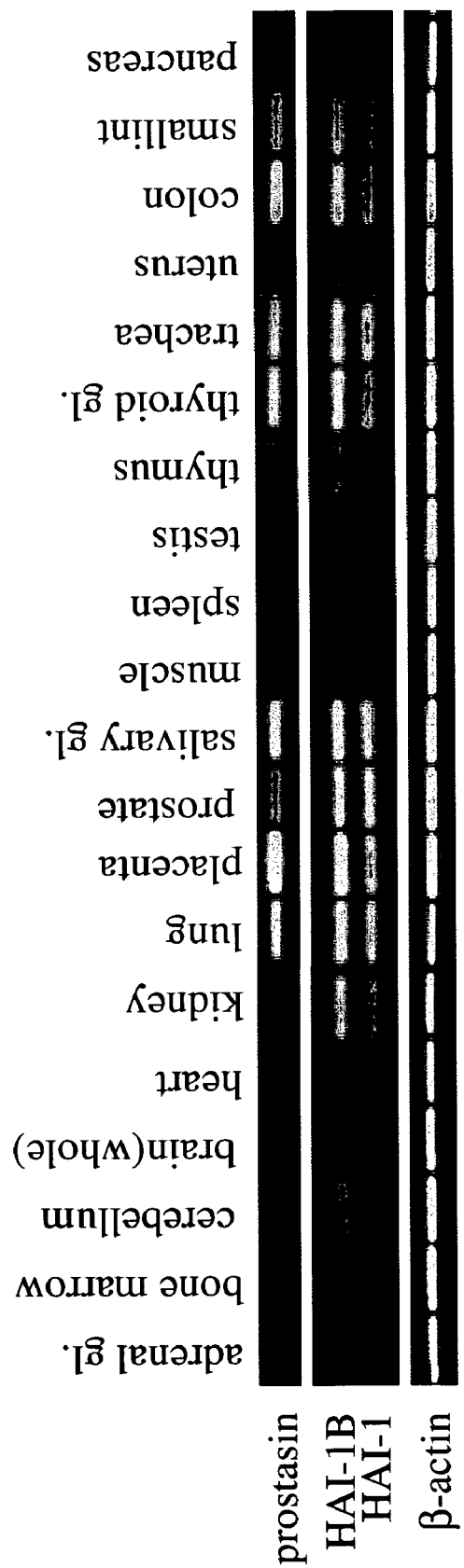
FIG._1

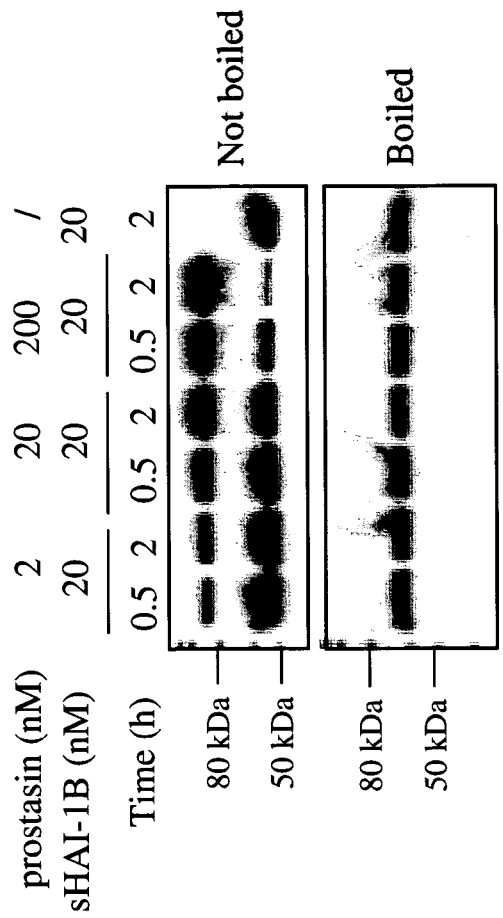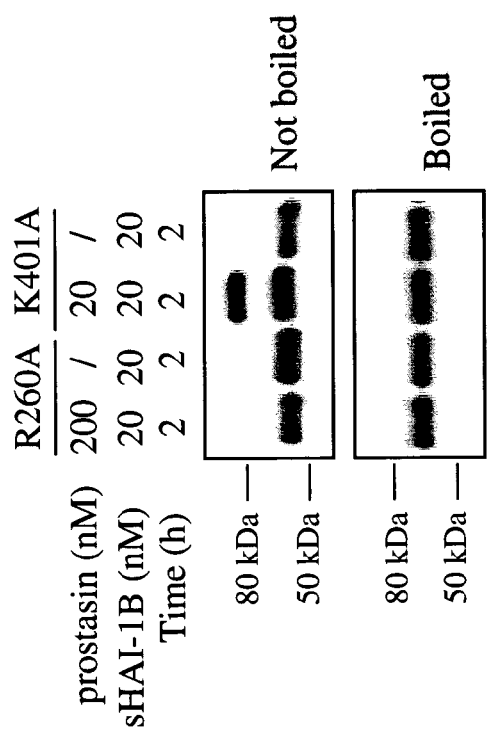
FIG._2

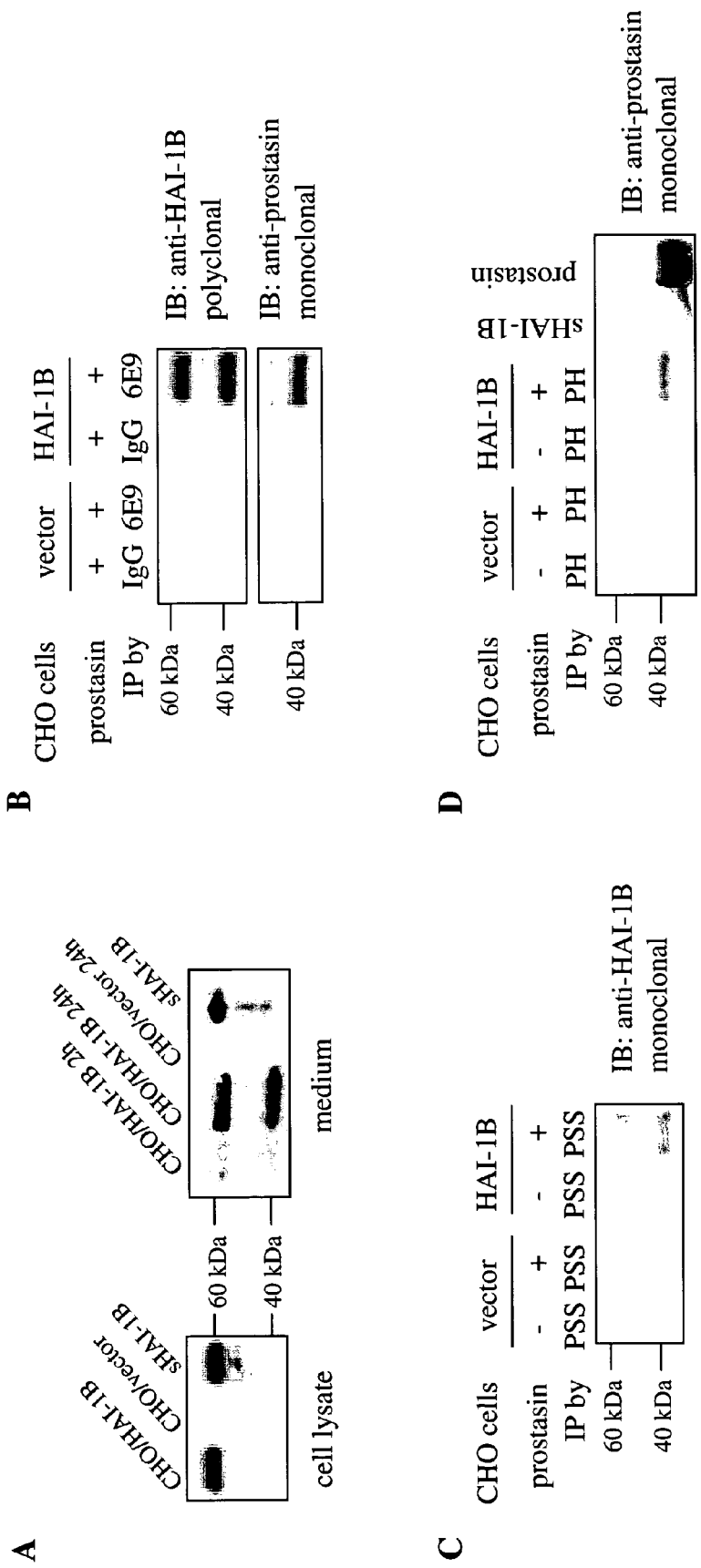
FIG._4

FIG. 5

MAQKGVLGPGQLGAVAILLYLGLLRSGTGAEGAEAPCGVA
PQARITGGSS AVAGQWPWQVSITYEGVHVCGGSLVSEQWV
LSAAHCFPSEHHKEAYEVKLGAHQLDSYSEDAKVSTLKDIIP
HPSYLQEGSQGDIALLQLSRPITFSRYIRPICLPAANASFPNGL
HCTVTGWGHVAPSVSLLTPKPLQQLEVPLISRETCNCLYNID
AKPEEPHFVQEDMVCAGYVEGGKDACQGDSGGPLSCPVEG
LWYLTGIVSWGDACGARNRPGVYTLASSYASWIQSKVTELQ
PRVVPQTQESQPDSNLCGSHLAFSSAPAQGLLRPILFLPLGLAL
GLLSPWLSEH (SEQ ID NO:1)

FIG._6

TEDYCLASNKVGRCRGSFPRWYYDPTEQICKSFV
YGGCLGNKNNYLREECILACRGV (SEQ ID NO:2)

METHODS AND COMPOSITIONS FOR MODULATING PROSTASIN

RELATED APPLICATIONS

This application is a non-provisional application filed under 37 CFR 1.53(b)(1), claiming priority under 35 USC 119(e) to provisional application No. 60/654,918 filed Feb. 22, 2005, the contents of which are incorporated herein by reference.

TECHNICAL FIELD

The present invention relates generally to the fields of molecular biology and growth factor regulation. More specifically, the invention concerns modulators of prostasin, and uses of said modulators.

BACKGROUND

Prostasin is a glycosylphosphatidylinositol-anchored, trypsin-like serine protease expressed on the surface of epithelial cells (Yu, Chao et al. 1994; Chen, Skinner et al. 2001). Mature prostasin is generated by a specific cleavage between $Arg^{12}$ and $Ile^{13}$, and consists of a 12-amino acid light chain disulfide-linked to a 299-amino acid protease domain (Yu, Chao et al. 1995). Prostasin was first purified as a soluble enzyme from human seminal fluid, suggesting that the membrane-anchored form undergoes shedding (Yu, Chao et al. 1994). The specific physiological functions and substrates of prostasin continue to be investigated. However, studies suggest important roles in regulating epithelial sodium channel (ENaC) in airway epithelia (Adachi, Kitamura et al. 2001; Donaldson, Hirsh et al. 2002; Tong, Illek et al. 2004). Using microarray technology, prostasin was detected more strongly in cancerous ovarian epithelial cells than in normal ovarian tissue. Increased prostasin serum level in patients, in combination with cancer antigen-125 (CA-125), could be a potential serum marker for ovarian cancer (Mok, Chao et al. 2001). However, prostasin expression is significantly down-regulated in high-grade or hormone-refractory prostate tumors and is lost in highly invasive human and mouse prostate cancer cell lines (Chen, Hodge et al. 2001; Takahashi, Suzuki et al. 2003). It may serve as an invasion suppressor for human prostate and breast cancers since the transfection of prostasin cDNA reduced in vitro invasiveness of prostate carcinoma cell lines (Chen, Hodge et al. 2001), as well as breast cancer cell lines (Chen and Chai 2002). A prostasin-binding protein was found in human and mouse seminal fluid and identified as protease nexin-1 (PN-1[1]) (Chen, Skinner et al. 2001; Chen, Zhang et al. 2004), a secreted serine protease inhibitor expressed in a variety of cell types (Bouton, Richard et al. 2003; Richard, Arocas et al. 2004). PN-1 formed an SDS-, heat-stable complex with prostasin and exhibited inhibitory activity towards prostasin with unclear potency (Chen, Zhang et al. 2004). However, PN-1 was not found forming a stable complex with prostasin in the extracts of some prostasin abundant tissues such as prostate, lung and salivary glands (Chen, Skinner et al. 2001), suggesting that additional prostasin inhibitors might exist.

[1] Abbreviations: PN-1, protease nexin-1; HAI-1/1B, hepatocyte growth factor activator inhibitor-1 and/or 1B; CHO, Chinese hamster ovary; KD1 and KD2, N- and C-terminal Kunitz domain of HAI-1B; sHAI-1B, soluble form of HAI-1B encompassing the extracellular domain; TT buffer, 20 mM Tris.Cl, pH 9.0 containing 0.01% Triton X-100.

Hepatocyte growth factor activator inhibitor-1B (HAI-1B) is a splicing isoform of HAI-1, a bi-Kunitz type serine protease inhibitor found mainly in epithelium (Kataoka, Suganuma et al. 1999; Itoh, Yamauchi et al. 2000). HAI-1 and/or HAI-1B (referred to herein as HAI-1/1B) is thought to be involved in tissue regeneration and tumorigenesis by inhibiting the activation of pro-HGF. Enhanced expression of HAI-1 was noted in regenerating epithelial cells such as the regenerative colon epithelium of acetic acid-induced mouse colitis models (Itoh, Kataoka et al. 2000), indicating a possible role in regulating the level of HGF activation. In agreement with this hypothesis, HAI-1 expression in colorectal mucosa was down-regulated in adenocarcinoma (Kataoka, Uchino et al. 1998; Kataoka, Hamasuna et al. 2000), where pro-HGF processing is enhanced (Kataoka, Hamasuna et al. 2000). HAI-1/1B consists of an N-terminal Kunitz domain (KD1), a low density lipoprotein receptor (LDLR)-like domain, a C-terminal Kunitz domain (KD2), and transmembrane and cytoplasmic domains (Shimomura, Denda et al. 1997). KD1 is thought to be responsible for the inhibitory activity according to mutagenesis studies (Denda, Shimomura et al. 2002; Kirchhofer, Peek et al. 2003). HAI-1/1B is synthesized as a transmembrane protein on the cell surface, and appears to be subsequently secreted by shedding (Shimomura, Denda et al. 1997; Shimomura, Denda et al. 1999). The shed form of HAI-1/1B is active in inhibiting HGF activator (HGFA) (Shimomura, Denda et al. 1997) and matriptase (Lin, Anders et al. 1999), both of which are pro-HGF activators. In addition, matriptase has extracellular matrix-degrading activity and possibly plays a role in breast cancer invasion (Lin, Wang et al. 1997). Matriptase was purified from human breast milk in complex with HAI-1/1B (Lin, Anders et al. 1999), indicating that HAI-1/1B is an important regulator of matriptase. Membrane bound HAI-1 is able to complex with active HGFA. The complex is quickly released from the cell surface upon treatment with phorbol 12-myristate 13-acetate (PMA) or interleukin-1B (IL-1B) in a metalloproteinase-dependent manner (Kataoka, Shimomura et al. 2000). Since HGFA could be recovered from the complex and maintained its activity, HAI-1 may serve as a reservoir for HGFA besides being an inhibitor of it. HAI-1B has a 16-amino acid insertion after the first Kunitz domain of HAI-1 (Kirchhofer, Peek et al. 2003). No significant differences between the two splice variants have been found in terms of tissue distribution, enzymatic activity or specificity.

We identify herein physiological prostasin inhibitors based at least in part on analyzing gene expression data with the assumption that prostasin and its cognate inhibitor(s) are co-expressed. This assumption is supported by observations of co-expression of other pairs of effector molecules and their endogenous inhibitors. For example, granzyme B has been found to be expressed in the same cells as its inhibitor PI-9 (SERPINB9) in humans (Muthukumar, Ding et al. 2003) and Spi6 in mice (Phillips, Opferman et al. 2004). Co-expression of the endogenous inhibitor may serve a protective role in host cells against the proteolytic effects of the serine protease. Similarly, quantitative correlation of expression has been found between matrix metalloproteinase 1 (MMP-1) and its inhibitor TIMP-1 in myocardium (Tyagi, Kumar et al. 1995), which is thought to serve as a mechanism to regulate the activity of the MMP-1.

The expression profile of prostasin in various pathological conditions as described above, coupled with its potential role in acting as a regulator of other growth factors the dysregulation of which might underlie carcinogenesis, suggests that modulation of prostasin's interaction with other cellular factors would be an efficacious therapeutic approach. In this regard, there is a clear need to identify prostasin's physiological modulator(s). The invention fulfills this need and provides other benefits.

All references cited herein, including patent applications and publications, are incorporated by reference in their entirety.

DISCLOSURE OF THE INVENTION

As described herein, a physiological inhibitor of prostasin is hepatocyte growth factor activator inhibitor 1 and 1B (HAI-1 and HAI-1B, respectively). Prostasin expression is distinctly associated with particular stages of progression or malignancy in multiple cancers. In addition, it is shown herein that the inhibitory activity of HAI-1 and HAI-1B against prostasin is located primarily in the first Kunitz domain (KD1), and that a polypeptide comprising this domain alone is capable of substantially inhibiting the biological activity of prostasin. Because differential expression of prostasin is believed to be associated with distinct stages in cancer progression, whether it is a decrease (e.g., in prostate and breast cancers) or increase (e.g., in ovarian cancer), the identification of a physiological inhibitor provides a heretofore unrecognized target for therapeutic intervention. The invention provides methods and compositions based at least in part on these findings, which are described in greater detail below. For example, because decreased expression of prostasin is associated with cancer progression in diseases such as prostate or breast cancer, it is believed that disrupting the inhibitory activity of HAI-1 or HAI-1B would reduce the deleterious pathological effects of downregulation of prostasin activity, and thereby be efficacious in treating such cancers. Conversely, in diseases in which progression is associated with increased prostasin expression, inhibition of prostasin activity by increased activity of HAI-1H/HAI-1B (or active fragment thereof, such as KD1) would be advantageous in treating the diseases. Therefore, it is clear, based on the data described herein, that HAI-1/HAI-1B and its interaction with and/or regulatory impact upon prostasin presents a unique and advantageous target for greater fine-tuning in designing prophylatic and/or therapeutic approaches against pathological conditions associated with abnormal or unwanted prostasin activity. Thus, the invention provides methods, compositions, kits and articles of manufacture for identifying and for using substances that are capable of modulating prostasin activity through modulation of the interaction of molecules physiologically involved in the regulation of prostasin activity.

Accordingly, in one aspect, the invention provides a method of screening for (or identifying) a candidate inhibitor (i.e., antagonist) substance that inhibits HAI-1/1B inhibition of prostasin, said method comprising: (a) contacting a candidate substance with a first sample comprising prostasin, HAI-1/1B, and a prostasin substrate, and (b) comparing amount of prostasin activity in the sample with amount of prostasin activity in a control sample that has not been contacted with said candidate substance, whereby an increase in amount of prostasin activity in the first sample compared to the control sample indicates that the candidate substance is capable of inhibiting HAI-1/1B inhibition of prostasin.

In another aspect, the invention provides a method of screening (or identifying) for a substance that blocks prostasin inhibition by HAI-1/1B, said method comprising screening for a substance that binds (preferably, but not necessarily, specifically) prostasin and/or HAI-1/1B wherein the substance blocks specific binding between prostasin and HAI-1/1B. In some embodiments, the substance competes with HAI-1/HAI-1B (specifically KD1 of HAI-1/HAI-1B) for binding to prostasin, wherein the substance does not substantially inhibit prostasin activity. In some embodiments, the substance competes with prostasin for binding to HAI-1/1B. In one embodiment, the substance comprises, consists or consists essentially of an amino acid sequence having at least about 60%, 70%, 80%, 90% but not 100% sequence similarity or identity with respect to KD1 of (SEQ ID NO:2; FIG. 6), wherein the substance is capable of binding to prostasin but has substantially diminished prostasin inhibitory activity. In one embodiment, the substance comprises, consists or consists essentially of an amino acid sequence having at least about 60%, 70%, 80%, 90% but not more than 95% sequence similarity or identity with respect to KD1 (SEQ ID NO:2; FIG. 6), wherein the substance is capable of binding to prostasin but has substantially diminished prostasin inhibitory activity. In one embodiment, the substance comprises, consists or consists essentially of an amino acid sequence having at least about 60%, 70%, 80%, 85% but not more than 90% sequence similarity or identity with respect to KD1 (SEQ ID NO:2; FIG. 6), wherein the substance is capable of binding to prostasin but has substantially diminished prostasin inhibitory activity.

As would be evident to one skilled in the art, screening assays consistent with those described above can also comprise a first step of screening based on a readout of prostasin-HAI-1/1B/KD1 complex formation to obtain a first set of candidate modulatory substances that interferen with the complex formation, optionally followed by a second step of screening based on ability of the first set of candidate modulatory substance to modulate inhibition of prostasin activity by HAI-1/1B. Suitable readouts can be any that would be evident to one skilled in the art, based on a knowledge of complex formation between prostasin and other molecules, and/or biological activities associated with prostasin. Prostasin complex formation can be measured using, for example, routine biochemical assays, e.g., gel electrophoresis, chromatography, NMR, etc.

In one aspect, the invention provides antagonists that disrupt physiological inhibition of prostasin (either resulting in increased or decreased prostasin activity). In one example, the invention provides a molecule that inhibits HAI-1/1B inhibition of prostasin activity. In another example, an antagonist molecule of the invention inhibits prostasin activity. The molecule can exert its antagonist function in any number of ways, including but not limited to binding to either prostasin or HAI-1/1B such that inhibitory effect of HAI-1/1B against prostasin is reduced, binding to prostasin and/or prostasin-HAI-1/1B complex such that prostasin activity is inhibited, etc.

In one aspect, the invention provides an antagonist of prostasin activity based on the discovery described herein that HAI-1/HAI-1B, and the domain comprising KD1 sequence, are inhibitors of prostasin that are capable of negatively regulating prostasin activity in a physiological setting. In one embodiment, the invention provides an antagonist of prostasin, said antagonist consisting or consisting essentially of at least a portion (including all) of KD1 (SEQ ID NO:2; FIG. 6). In one embodiment, an antagonist of the invention consists or consists essentially of a variant KD1 sequence having at least about 70%, 75%, 80%, 85%, 90%, 95%, 97%, 98%, 99% sequence identity with wild type KD1 (SEQ ID NO:2; FIG. 6), wherein said variant sequence has at least about 50%, 60%, 70%, 80%, 90% of the inhibitory activity of wild type human KD1 (encoded by SEQ ID NO:2) against prostasin activity. In one embodiment, an antagonist of the invention consists or consists of a variant KD1 sequence having between about 70% and 99%, about 75% and 98%, about 80% and 97%, 85% and 95% sequence identity with wild type KD1 (SEQ ID NO:2; FIG. 6), wherein said variant sequence has at least about 50%, 60%, 70%, 80%, 90% of the inhibitory activity of wild type human KD1 (encoded by SEQ ID NO:2) against prostasin activity.

In some embodiments, an antagonist of the invention is or comprises a peptide, antibody, antibody fragment, aptamer, or a combination thereof. Antagonists as described herein can be routinely obtained using techniques known in the art (including those described in greater detail below) based on the discovery of the physiological relationship of HAI-1/1B (specifically KD1) and prostasin as described herein.

In one aspect, the invention provides a HAI-1/1B or KD1 mutant capable of substantially binding prostasin but has decreased inhibitory activity against prostasin compared to wild type HAI-1/1B or KD1, e.g. an HAI-1/1B or KD1 polypeptide/peptide exhibiting a reduction, but not an absence, of prostasin inhibitory activity. In one embodiment, an antagonist of the invention is capable of modulating cellular and/or tissue effects associated with prostasin expression levels.

In some embodiments, an antagonist of the invention (which can be an antagonist of HAI-1/1B/KD1 inhibition of prostasin, or an antagonist of prostasin enzymatic activity, as described in greater detail above) is obtained by a screening or identification method of the invention as described herein.

In one aspect, an antagonist molecule of the invention is linked to a toxin such as a cytotoxic agent. These molecules can be formulated or administered in combination with an additive/enhancing agent, such as a radiation and/or chemotherapeutic agent.

In one aspect, the invention provides an antagonist molecule capable of enhancing physiological levels of prostasin activity, wherein said molecule interferes with HAI-1/1B/KD1 interaction with prostasin, and wherein the molecule is or comprises a peptide, antibody, antibody fragment, aptamer, or a combination thereof. For example, the molecule may comprise, consist, or consist essentially of a fragment, or variant thereof, of HAI-1/1B/KD1, wherein said fragment is capable of binding to prostasin but does not substantially inhibit prostasin enzymatic activity. In one embodiment, said molecule is capable of competitively inhibiting binding of wild type HAI-1/1B/KD1 and prostasin. In one embodiment, an antagonist molecule of the invention is an antibody that interferes with formation of a complex comprising prostasin and HAI-1, HAI-1B and/or KD1. In one embodiment, an antagonist molecule of the invention is prostasin or variant thereof (including any of those defined below), wherein the prostasin or variant thereof is capable of binding to HAI-1/1B/KD1 but has substantially reduced wild type prostasin enzymatic activity.

In one aspect, the invention provides an antagonist molecule that inhibits prostasin activity. For example, such antagonist molecule may comprise a HAI-1/1B/KD1 fragment, or variant thereof, that is capable of binding to prostasin to inhibit prostasin enzymatic activity.

The invention also provides methods and compositions useful for modulating disease states associated with dysregulation of prostasin activity. Thus, in one aspect, the invention provides a method of modulating prostasin activity in a subject, said method comprising administering to the subject an antagonist molecule of the invention (e.g., an antagonist molecule, as described herein, that inhibits HAI-1/1B/KD1 inhibition of prostasin), whereby prostasin activity is modulated. In one embodiment, said molecule is a HAI-1/1B/KD1 antagonist that inhibits HAI-1/1B/KD1 inhibition of prostasin. In one embodiment, said molecule is an antagonist molecule that inhibits prostasin activity (as described herein). In one aspect, the invention provides a method of treating a pathological condition associated with downregulation of prostasin in a subject, said method comprising administering to the subject an antagonist molecule of the invention, whereby prostasin activity is increased. In one aspect, the invention provides a method of treating a pathological condition associated with upregulation of prostasin in a subject, said method comprising administering to the subject an antagonist molecule of the invention that inhibits prostasin activity, whereby prostasin activity is decreased.

Prostasin is involved in multiple biological and physiological functions, including, for example, regulation of epithelial sodium channel (e.g., in airway epithelia), cancer progression in ovarian cancer, prostate cancer and breast cancer. For example, prostasin down-regulation is associated with high-grade or hormone-refractory prostate tumors and is lost in highly invasive prostate cancer cells. It is also implicated in suppression of invasion for prostate and breast cancers. Thus, in another aspect, the invention provides a method of reducing physiological inhibition of prostasin activity in a subject having a pathological condition associated with down-regulation of prostasin activity, said method comprising administering to the subject an antagonist of the invention, whereby prostasin activity is enhanced. In yet another aspect, the invention provides a method of treating a subject having a pathological condition associated with dysregulated sodium channel function and sub-normal prostasin activity, said method comprising administering to the subject an antagonist of the invention, whereby prostasin activity is enhanced. In yet another aspect, the invention provides a method of treating a subject having a pathological condition associated with dysregulated sodium channel function and supra-normal prostasin activity, said method comprising administering to the subject a molecule of the invention that inhibits prostasin activity, whereby prostasin activity is decreased. In yet another aspect, the invention provides a method of treating a subject having cancer at a stage associated with sub-normal prostasin activity, said method comprising administering to the subject an antagonist of the invention, whereby prostasin activity is enhanced. In one embodiment, the cancer is high-grade prostate cancer. In one embodiment, the cancer is hormone-refractory prostate cancer. In one embodiment, the cancer is invasive prostate cancer. In one embodiment, the cancer is invasive breast cancer. In one embodiment, the cancer is metastatic breast cancer. In one embodiment, the antagonist molecule suppresses cancer cell invasion. In one embodiment, the antagonist molecule suppresses cancer cell metastasis. In one embodiment, the antagonist molecule suppresses tumor progression. In yet another aspect, the invention provides a method of treating a subject having cancer associated with supra-normal prostasin activity, said method comprising administering to the subject an antagonist molecule of the invention that inhibits prostasin activity, whereby prostasin activity is decreased. In one embodiment, the cancer is ovarian cancer. In one embodiment, the antagonist molecule suppresses cancer cell invasion. In one embodiment, the antagonist molecule suppresses cancer cell metastasis. In one embodiment, the antagonist molecule suppresses tumor progression. In one aspect, the invention provides a method of inhibiting cancer, said method comprising contacting a cell or tissue with an effective amount of an antagonist of the invention, whereby cell proliferation associated with prostasin activity is inhibited.

In one aspect, the invention provides a method of treating a pathological condition associated with dysregulation of prostasin in a subject, said method comprising administering to the subject an effective amount of an antagonist of the invention, whereby said condition is treated.

In one aspect, the invention provides a method of inhibiting the growth of a cell that expresses and/or is regulated by prostasin and/or HAI-1/1B, or both, said method comprising contacting said cell with an antagonist of the invention thereby causing an inhibition of growth of said cell.

In one aspect, the invention provides a method of therapeutically treating a mammal having a cancerous tumor comprising a cell that expresses prostasin and/or HAI-1/1B, said method comprising administering to said mammal an effective amount of an antagonist of the invention, thereby effectively treating said mammal.

In one aspect, the invention provides a method for treating or preventing a cell proliferative disorder associated with dysregulated activity of prostasin and/or HAI-1/1B, or both, said method comprising administering to a subject an effective amount of an antagonist of the invention, thereby effectively treating or preventing said cell proliferative disorder. In one embodiment, said proliferative disorder is cancer.

In one aspect, the invention provides a method for regulating growth of a cell, wherein growth of said cell is at least in part dependent upon activity of prostasin and/or HAI-1/1B, or both, said method comprising contacting said cell with an effective amount of an antagonist of the invention, thereby modifying the growth rate of said cell.

In one aspect, the invention provides a method of treating a tumor in a mammal, wherein the growth of said tumor is at least in part dependent upon activity of prostasin and/or HAI-1/1B, or both, said method comprising contacting said cell with an effective amount of an antagonist of the invention, thereby effectively treating said tumor.

Methods of the invention can be used to affect any suitable pathological state, for example, cells and/or tissues associated with dysregulation of physiological prostasin activity. In one embodiment, a cell that is targeted in a method of the invention is a cancer cell. For example, a cancer cell can be one selected from the group consisting of a breast cancer cell, a colorectal cancer cell, a lung cancer cell, a papillary carcinoma cell (for e.g., of the thyroid gland), a colon cancer cell, a pancreatic cancer cell, an ovarian cancer cell, a cervical cancer cell, a central nervous system cancer cell, an osteogenic sarcoma cell, a prostate cancer cell, a renal carcinoma cell, a hepatocellular carcinoma cell, a bladder cancer cell, a gastric carcinoma cell, a head and neck squamous carcinoma cell, a melanoma cell and a leukemia cell. In one embodiment, a cell that is targeted in a method of the invention is a hyperproliferative and/or hyperplastic cell. In one embodiment, a cell that is targeted in a method of the invention is a dysplastic cell. In one embodiment, a cell that is targeted in a method of the invention is an invasive cell. In yet another embodiment, a cell that is targeted in a method of the invention is a metastatic cell.

Methods of the invention can further comprise additional treatment steps. For example, in one embodiment, a method further comprises a step wherein a targeted cell and/or tissue (e.g., a cancer cell) is exposed to radiation treatment or a chemotherapeutic agent.

As described herein, dysregulation of prostasin activity leads to numerous pathological conditions. Accordingly, in one embodiment of methods of the invention, a cell that is targeted (e.g., a cancer cell) is one in which prostasin activity level is different compared to a normal cell of the same tissue origin. In one embodiment, a method of the invention causes the death of a targeted cell.

Dysregulation of prostasin activity can result from a number of cellular changes, including, for example, overexpression or underexpression of prostasin and/or its physiological inhibitor HAI-1/1B. Accordingly, in some embodiments, a method of the invention comprises targeting a cell wherein activity of prostasin and/or HAI-1/1B, or both, is different in said cell (e.g., a cancer cell) as compared to a normal cell of the same tissue origin.

In one aspect, the invention provides compositions comprising one or more antagonist molecules of the invention and a carrier. In one embodiment, the carrier is pharmaceutically acceptable.

In one aspect, the invention provides nucleic acids encoding an antagonist molecule of the invention. In one embodiment, a nucleic acid of the invention encodes an antagonist molecule which is or comprises a polypeptide (e.g., an oligopeptide). In one embodiment, the polypeptide or oligopeptide comprises the sequence of KD1 (SEQ ID NO:2; FIG. 6), or variant thereof. In one embodiment, a nucleic acid of the invention encodes an antagonist molecule which is or comprises an antibody or fragment thereof.

In one aspect, the invention provides vectors comprising a nucleic acid of the invention.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, *E. coli*. In one embodiment, a host cell is a eukaryotic cell, for example a mammalian cell such as Chinese Hamster Ovary (CHO) cell.

In one aspect, the invention provides methods for making an antagonist molecule of the invention. For example, the invention provides a method of making an antagonist which is or comprises an antibody (or fragment thereof), said method comprising expressing in a suitable host cell a recombinant vector of the invention encoding said antibody (or fragment thereof), and recovering said antibody. In another example, the invention provides a method of making an antagonist molecule which is or comprises a polypeptide (such as an oligopeptide), said method comprising expressing in a suitable host cell a recombinant vector of the invention encoding said polypeptide (such as an oligopeptide), and recovering said polypeptide (such as an oligopeptide).

In one aspect, the invention provides an article of manufacture comprising a container; and a composition contained within the container, wherein the composition comprises one or more antagonist molecules of the invention. In one embodiment, the composition comprises a nucleic acid of the invention. In one embodiment, a composition comprising an antagonist molecule further comprises a carrier, which in some embodiments is pharmaceutically acceptable. In one embodiment, an article of manufacture of the invention further comprises instructions for administering the composition (e.g., the antagonist molecule) to a subject.

In one aspect, the invention provides a kit comprising a first container comprising a composition comprising one or more antagonist molecules of the invention; and a second container comprising a buffer. In one embodiment, the buffer is pharmaceutically acceptable. In one embodiment, a composition comprising an antagonist molecule further comprises a carrier, which in some embodiments is pharmaceutically acceptable. In one embodiment, a kit further comprises instructions for administering the composition (e.g., the antagonist molecule) to a subject.

BRIEF DESCRIPTION OF THE DRAWINGS

FIG. 1. mRNA levels of prostasin, HAI-1 and HAI-1B in normal human tissues. Reverse transcription-PCR of total tissue mRNA was carried out to examine the expression of prostasin, HAI-1 and HAI-1B in normal human tissues. The primer sets for HAI-1 and HAI-1B allowed amplification of the region encompassing the splice site, so that the two different PCR products (269 base pairs for HAI-1B and 221 base pairs for HAI-1) were generated. β-actin served as a control. Adrenal gl., adrenal gland; salivary gl., salivary gland; thyroid gl., thyroid gland; smallint, small intestine.

FIG. 2. Prostasin forms complexes with sHAI-1B. Prostasin of indicated concentration was incubated with 20 nM wildtype sHAI-1B (A) or mutant sHAI-1B (B) at 37° C. for 0.5 or 2 h. The reactions were stopped by addition of SDS sample buffer with DTT. 30 µl of each sample was boiled or not boiled (as indicated) followed by immunoblotting analysis using anti-HAI-1B polyclonal antibody.

FIG. 4. Prostasin/HAI-1B interactions in the CHO/HAI-1B stable cell culture. A: HAI-1B is expressed on the cell membrane and spontaneously shed. CHO cells transfected with HAI-1B (CHO/HAI-1B) or vector alone (CHO/vector) were grown in serum-free medium for 2 h and 24 h. Both the cell extract and medium were subjected to immunoblotting analysis using anti-HAI-1B polyclonal antibody. sHAI-1B, 10 ng purified sHAI-1B. B, C, D: Confluent CHO/HAI-1B or CHO/vector cells were incubated with or without 200 ng/ml prostasin in serum-free medium for 2 hours. The prostasin: HAI-1B complexes were co-immunoprecipitated from the medium (B and C) or the cell lysate (D). The last two lanes in D are 25 ng of sHAI-1B and 25 ng of prostasin, respectively. IP, immunoprecipitation; IB, immunoblotting; IgG, mouse IgG (control); 6E9, anti-HAI-1B monoclonal antibody; PSS, anti-prostasin polyclonal antibody; PH, anti-HAI-1B polyclonal antibody.

FIG. 5 depicts amino acid sequence of wild type human prostasin (SEQ ID NO: 1).

FIG. 6 depicts amino acid sequence of an illustrative embodiment of KD1 from wild type HAI-1/1B (SEQ ID NO:2).

MODES FOR CARRYING OUT THE INVENTION

Figure 3:
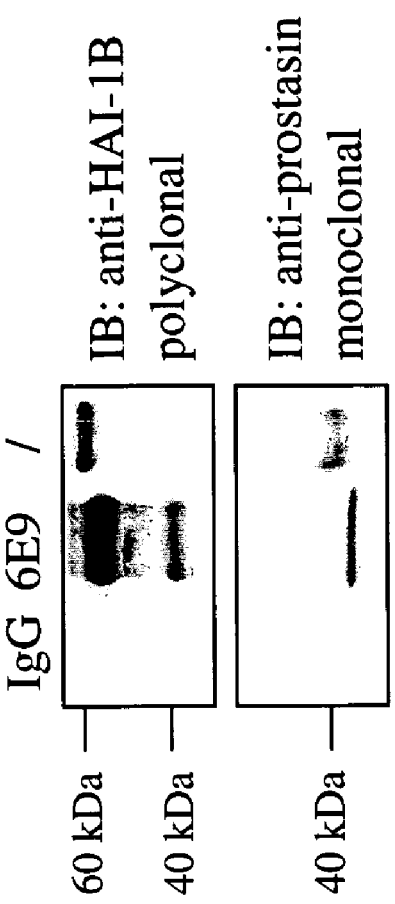
FIG. 3. Prostasin forms complexes with HAI-1/1B in OVCAR3 cell medium. A: Reverse transcription-PCR of total mRNA was carried out to examine the expression of prostasin, HAI-1 and HAI-1B in OVCAR3 cells. B: OVCAR3 cells were grown in 250 ml DMEM medium plus 10% serum in a 2-liter roller bottle. The medium was allowed to bind to the indicated antibody-coupled resin. The bound proteins were eluted and analyzed by immunoblotting. 10 ng sHAI-1B (upper panel) or 25 ng prostasin (lower panel) were loaded in the last lanes. IB, immunoblotting; IgG, mouse IgG (control); 6E9, anti-HAI-1B monoclonal antibody.

The invention provides methods, compositions, kits and articles of manufacture comprising modulators of prostasin function, including methods of using such modulators.

Details of these methods, compositions, kits and articles of manufacture are provided herein.

General Techniques The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

Definitions

The term "prostasin" as used herein encompasses native sequence polypeptides, polypeptide variants and fragments of a native sequence polypeptide and polypeptide variants (which are further defined herein) that is capable of prostasin enzymatic activity in a manner similar to wild type prostasin. The prostasin polypeptide described herein may be that which is isolated from a variety of sources, such as from human tissue types or from another source, or prepared by recombinant or synthetic methods. The terms "prostasin", "prostasin polypeptide", "prostasin enzyme", and "prostasin protein" also include variants of a prostasin polypeptide as disclosed herein.

A "native sequence prostasin polypeptide" comprises a polypeptide having the same amino acid sequence as the corresponding prostasin polypeptide derived from nature. In one embodiment, a native sequence prostasin polypeptide comprises the amino acid sequence of SEQ ID NO:1 (see FIG. 5). Such native sequence prostasin polypeptide can be isolated from nature or can be produced by recombinant or synthetic means. The term "native sequence prostasin polypeptide" specifically encompasses naturally-occurring truncated or secreted forms of the specific prostasin polypeptide (e.g., an extracellular domain sequence), naturally-occurring variant forms (e.g., alternatively spliced forms) and naturally-occurring allelic variants of the polypeptide. "Prostasin polypeptide variant", or variations thereof, means a prostasin polypeptide, generally an active prostasin polypeptide, as defined herein having at least about 80% amino acid sequence identity with a native sequence prostasin polypeptide sequence as disclosed herein. Such prostasin polypeptide variants include, for instance, prostasin polypeptides wherein one or more amino acid residues are added, or deleted, at the N- or C-terminus of a native amino acid sequence. Ordinarily, a prostasin polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a native sequence prostasin polypeptide sequence as disclosed herein. Ordinarily, prostasin variant polypeptides are at least about 10 amino acids in length, alternatively at least about 20, 30,40, 50, 60, 70, 80, 90, 100, 110, 120, 130, 140, 150, 160, 170, 180, 190, 200, 210, 220, 230, 240, 250, 260, 270, 280, 290, 300, 310, 320, 330,340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, prostasin variant polypeptides will have no more than one conservative amino acid substitution as compared to a native prostasin polypeptide sequence, alternatively no more than 2, 3, 4, 5, 6, 7, 8, 9, or 10 conservative amino acid substitution as compared to the native prostasin polypeptide sequence. "Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNAS- TAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, as described in U.S. Pat. No. 6,828,146.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector. "Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured. The use of the phrase "antibody and fragment thereof", and grammatical variations of this phrase, does not relate to the definition of "antibody" as set forth in this paragraph. Therefore, unless indicated otherwise herein, the term "antibody" by itself includes an antibody fragment.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. In some embodiments, blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega11 (see, e.g., Agnew, *Chem Intl. Ed. Engl.*, 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; other antiandrogens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRRH (e.g., ABARELIX®); lapatinib ditosylate (an ErbB-2 and EGFR dual tyrosine kinase small-molecule inhibitor also known as GW572016); COX-2 inhibitors such as celecoxib (CELEBREX®; 4-(5-(4-methylphenyl)-3-(trifluoromethyl)-1H-pyrazol-1-yl)benzenesulfonamide; and pharmaceutically acceptable salts, acids or derivatives of any of the above.

A "growth inhibitory agent" when used herein refers to a compound or composition which inhibits growth of a cell whose growth is dependent upon prostasin activity either in vitro or in vivo. Thus, the growth inhibitory agent may be one which significantly reduces the percentage of prostasin-dependent cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells. "Doxorubicin" is an anthracycline antibiotic. The full chemical name of doxorubicin is (8S-cis)-10-[(3-amino-2,3, 6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

Compositions and Methods of the Invention

A. Antibodies

In one embodiment, the present invention provides antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N$=C=NR, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ¹⁄₁₀ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va. USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Pluckthun, *Immunol. Revs.* 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.* 151:2623 (1993)).

It is further important that antibodies be humanized with retention of high binding affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggemann et al., *Year in Immuno.* 7:33 (1993); U.S. Pat. Nos. 5,545,806, 5,569,825, 5,591,669 (all of GenPharm); 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of protasin, HAI-1/1B and/or prostasin:HAI-1/1B complex as described herein. Other such antibodies may combine a binding site on these entities with a binding site for another polypeptide. Alternatively, an antibody arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the prostasin and/or HAI-1/1B-expressing and/or binding cell. Bispecific antibodies may also be used to localize cytotoxic agents to cells which express and/or bind prostasin, HAI-1/1B and/or prostasin: HAI-1/1B complex. These antibodies possess a polypeptide binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites.

Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-$(X1)_n$-VD2-$(X2)_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

9. Immunoconjugates

The invention also pertains to immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19): 1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al. (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a huCD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol)propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothecene, and CC1065, and the derivatives of these toxins that have toxin activity, are also contemplated herein.

Maytansine and Maytansinoids

In one embodiment, an antibody (full length or fragments) of the invention is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3\times10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid Conjugates (Immunoconjugates)

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as his (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene) Particularly preferred coupling agents include N-succinimidyl-3-(2-pyridyldithio)propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In one embodiment, the linkage is formed at the C-3 position of maytansinol or a maytansinol analogue.

Calicheamicin

Another immunoconjugate of interest comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $.Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal,CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCI), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene) For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody.

$$Ab\text{-}(L\text{-}D)_p \qquad\qquad I$$

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody drug conjugates of the invention may also be produced by modification of the antibody to introduce electrophilic moieties, which can react with nucleophilic subsituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, *Bioconiugate Techniques*). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxy-late, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

B. Binding Oligopeptides

Binding oligopeptides of the invention are oligopeptides that bind, preferably specifically, to prostasin, HAI-1/1B and/or prostasin: HAI-1/1B complex as described herein. Binding oligopeptides may be chemically synthesized using known oligopeptide synthesis methodology or may be prepared and purified using recombinant technology. Binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42,43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a polypeptide as described herein. Binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750, 373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol. Meth.*, 102:259-274 (1987); Schoofs et al., *J. Immunol.*, 140:611-616 (1988), Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) *Science*, 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) *Proc. Natl. Acad. Sci. USA*, 87:6378) or protein (Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363) libraries on phage have been used for screening millions of polypeptides or oligopeptides for ones with specific binding properties (Smith, G. P. (1991) *Current Opin. Biotechnol.*, 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., *Gene*, 215: 439 (1998); Zhu et al., *Cancer Research*, 58(15): 3209-3214 (1998); Jiang et al., *Infection & Immunity*, 65(11): 4770-4777 (1997); Ren et al., *Gene*, 195(2):303-311 (1997); Ren, *Protein Sci.*, 5: 1833 (1995); Efimov et al., *Virus Genes*, 10: 173 (1995)) and T7 phage display systems (Smith and Scott, *Methods in Enzymology*, 217: 228-257 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphlylococcus aureus* protein A as an affinity tag has also been reported (Li et al. (1998) Mol Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. Binding Small Molecules

Binding small molecules are preferably organic molecules other than oligopeptides or antibodies as defined herein that bind, preferably specifically, to prostasin, HAI-1/1B and/or prostasin:HAI-1/1B complex as described herein. Binding organic small molecules may be identified and chemically synthesized using known methodology (see, e.g., PCT Publication Nos. WO00/00823 and WO00/39585). Binding organic small molecules are usually less than about 2000 daltons in size, alternatively less than about 1500, 750, 500, 250 or 200 daltons in size, wherein such organic small molecules that are capable of binding, preferably specifically, to a polypeptide as described herein may be identified without undue experimentation using well known techniques. In this regard, it is noted that techniques for screening organic small molecule libraries for molecules that are capable of binding to a polypeptide target are well known in the art (see, e.g., PCT Publication Nos. WO00/00823 and WO00/39585). Binding organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

D. Screening for Antibodies, Binding Oligopeptides and Binding Small Molecules with the Desired Properties Techniques for generating antibodies, oligopeptides and small moleculesof the invention have been described above. One may further select antibodies, oligopeptides or other small molecules with certain biological characteristics, as desired.

The growth inhibitory effects of an antibody, oligopeptide or other small molecule of the invention may be assessed by methods known in the art, e.g., using cells which express prostasin and/or HAI-1/1b either endogenously or following transfection with the respective gene(s). For example, appropriate tumor cell lines, and prostasin and/or HAI-1/1B polypeptide-transfected cells may be treated with a monoclonal antibody, oligopeptide or other small molecule of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an antibody, binding oligopeptide or binding small molecule of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. The tumor cell may be one that overexpresses a prostasin and/or HAI-1/1B polypeptide. The antibody, binding oligopeptide or binding organic small molecule will inhibit cell proliferation of a prostasin and/or HAI-1/1B-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the antibody at about 1 µg/kg to about 100 mg/kg body weight results in reduction in tumor size or reduction of tumor cell proliferation within about 5 days to 3 months from the first administration of the antibody, preferably within about 5 to 30 days.

To select for an antibody, binding oligopeptide or binding organic small molecule which induces cell death, loss of membrane integrity as indicated by, e.g., propidium iodide (PI), trypan blue or 7AAD uptake may be assessed relative to control. A PI uptake assay can be performed in the absence of complement and immune effector cells. Prostasin and/or HAI-1/1B polypeptide-expressing tumor cells are incubated with medium alone or medium containing the appropriate antibody (e.g, at about 10 µg/ml), binding oligopeptide or binding organic small molecule. The cells are incubated for a 3-day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those antibodies, binding oligopeptides or binding organic small molecules that induce statistically significant levels of cell death as determined by PI uptake may be selected as cell death-inducing antibodies, binding oligopeptides or binding organic small molecules.

To screen for antibodies, oligopeptides or other organic small molecules which bind to an epitope on a polypeptide bound by an antibody of interest, a routine cross-blocking assay such as that described in *Antibodies. A Laboratory Manual*, Cold Spring Harbor Laboratory, Ed Harlow and David Lane (1988), can be performed. This assay can be used to determine if a test antibody, oligopeptide or other organic small molecule binds the same site or epitope as a known antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a polypeptide can be used in competition assays with the test antibodies or with a test antibody and an antibody with a characterized or known epitope.

E. Antibody Dependent Enzyme Mediated Prodrug Therapy (ADEPT)

The antibodies of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 (1987)). Antibody-abzyme conjugates can be prepared as described herein for delivery of the abzyme to a tumor cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604-608 (1984).

F. Antibody Variants

In addition to the antibodies described herein, it is contemplated that antibody variants can be prepared. Antibody variants can be prepared by introducing appropriate nucleotide changes into the encoding DNA, and/or by synthesis of the desired antibody. Those skilled in the art will appreciate that amino acid changes may alter post-translational processes of the antibody, such as changing the number or position of glycosylation sites or altering the membrane anchoring characteristics.

Variations in the antibodies described herein can be made, for example, using any of the techniques and guidelines for conservative and non-conservative mutations set forth, for instance, in U.S. Pat. No. 5,364,934. Variations may be a substitution, deletion or insertion of one or more codons encoding the antibody that results in a change in the amino acid sequence as compared with the native sequence antibody or polypeptide. Optionally the variation is by substitution of at least one amino acid with any other amino acid in one or more of the domains of the antibody. Guidance in determining which amino acid residue may be inserted, substituted or deleted without adversely affecting the desired activity may be found by comparing the sequence of the antibody with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the parent sequence.

Antibody and polypeptide fragments are provided herein. Such fragments may be truncated at the N-terminus or C-terminus, or may lack internal residues, for example, when compared with a full length native antibody or protein. Certain fragments lack amino acid residues that are not essential for a desired biological activity of the antibody or polypeptide.

Antibody and polypeptide fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, antibody and polypeptide fragments share at least one biological and/or immunological activity with the native antibody or polypeptide disclosed herein.

In particular embodiments, conservative substitutions of interest are shown in the table below under the heading of preferred substitutions. If such substitutions result in a change in biological activity, then more substantial changes, denominated exemplary substitutions in this table, or as further described below in reference to amino acid classes, are introduced and the products screened.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |

-continued

| Original Residue | Exemplary Substitutions | Preferred Substitutions |
|---|---|---|
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the antibody or polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His(H)
Alternatively, naturally occurring residues may be divided into groups based on common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.
Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the antibody or polypeptide variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244:1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

Any cysteine residue not involved in maintaining the proper conformation of the antibody or polypeptide also may be substituted, generally with serine, to improve the oxidative stability of the molecule and prevent aberrant crosslinking. Conversely, cysteine bond(s) may be added to the antibody or polypeptide to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

G. Modifications of Antibodies and Polypeptides

Covalent modifications of antibodies and polypeptides are included within the scope of this invention. One type of covalent modification includes reacting targeted amino acid residues of an antibody or polypeptide with an organic derivatizing agent that is capable of reacting with selected side chains or the N- or C-terminal residues of the antibody or polypeptide. Derivatization with bifunctional agents is useful, for instance, for crosslinking antibody or polypeptide to a water-insoluble support matrix or surface for use in the method for purifying antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithiol]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the antibody or polypeptide included within the scope of this invention comprises altering the native glycosylation pattern of the antibody or polypeptide. "Altering the native glycosylation pattern" is intended for purposes herein to mean deleting one or more carbohydrate moieties found in native sequence antibody or polypeptide (either by removing the underlying glycosylation site or by deleting the glycosylation by chemical and/or enzymatic means), and/or adding one or more glycosylation sites that are not present in the native sequence antibody or polypeptide. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody or polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody or polypeptide (for O-linked glycosylation sites). The antibody or polypeptide amino acid sequence may optionally be altered through changes at the DNA level, particularly by mutating the DNA encoding the antibody or polypeptide at preselected bases such that codons are generated that will translate into the desired amino acids.

Another means of increasing the number of carbohydrate moieties on the antibody or polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the antibody or polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of antibody or polypeptide comprises linking the antibody or polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

The antibody or polypeptide of the present invention may also be modified in a way to form chimeric molecules comprising an antibody or polypeptide fused to another, heterologous polypeptide or amino acid sequence.

In one embodiment, such a chimeric molecule comprises a fusion of the antibody or polypeptide with a tag polypeptide which provides an epitope to which an anti-tag antibody can selectively bind. The epitope tag is generally placed at the amino- or carboxyl- terminus of the antibody or polypeptide. The presence of such epitope-tagged forms of the antibody or polypeptide can be detected using an antibody against the tag polypeptide. Also, provision of the epitope tag enables the antibody or polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the antibody or polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an antibody or polypeptide in place of at least one variable region within an Ig molecule. In one embodiment, the immunoglobulin fusion includes the hinge, $CH_2$ and $CH_3$, or the hinge, $CH_1$, $CH_2$ and $CH_3$ regions of an IgG1 molecule. For the production of immunoglobulin fusions see also U.S. Pat. No. 5,428,130 issued Jun. 27, 1995.

H. Preparation of Antibodies and Polypeptides

The description below relates primarily to production of antibodies and polypeptides by culturing cells transformed or transfected with a vector containing antibody- and polypeptide-encoding nucleic acid. It is, of course, contemplated that alternative methods, which are well known in the art, may be employed to prepare antibodies and polypeptides. For instance, the appropriate amino acid sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the antibody or polypeptide may be chemically synthesized separately and combined using chemical or enzymatic methods to produce the desired antibody or polypeptide.

1. Isolation of DNA Encoding Antibody or Polypeptide

DNA encoding antibody or polypeptide may be obtained from a cDNA library prepared from tissue believed to possess the antibody or polypeptide mRNA and to express it at a detectable level. Accordingly, human antibody or polypeptide DNA can be conveniently obtained from a cDNA library prepared from human tissue. The antibody- or polypeptide-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding antibody or polypeptide is to use PCR methodology [Sambrook et al., supra; Dieffenbach et al., *PCR Primer: A Laboratory Manual* (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for antibody or polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA ; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full-length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation regio (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody- or polypeptide-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265-278 [1988]); *Candida; Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated antibody or polypeptide are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibody or polypeptide production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding antibody or polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the antibody- or polypeptide-encoding DNA that is inserted into the vector. The signal sequence may be a prokaryotic signal equence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 November 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2 μplasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the antibody- or polypeptide-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the antibody- or polypeptide-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [de-Boer et al., *Proc. Natl. Acad. Sci. USA*, 80:21-25 (1983)]. Promoters for use in bacterial systems also will contain a Shine-Dalgarno (S.D.) sequence operably linked to the DNA encoding antibody or polypeptide.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Antibody or polypeptide transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the antibody or polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antibody or polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody or polypeptide.

Still other methods, vectors, and host cells suitable for adaptation to the synthesis of antibody or polypeptide in recombinant vertebrate cell culture are described in Gething et al., *Nature*, 293:620-625 (1981); Mantei et al., *Nature*, 281:40-46 (1979); EP 117,060; and EP 117,058.

4. Culturing the Host Cells

The host cells used to produce the antibody or polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.*102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence polypeptide or against a synthetic peptide based on the DNA sequence provided herein or against exogenous sequence fused to polypeptide DNA and encoding a specific antibody epitope.

6. Purification of Antibody and Polypeptide

Forms of antibody and polypeptide may be recovered from culture medium or from host cell lysates. If membrane-bound, it can be released from the membrane using a suitable detergent solution (e.g. Triton-X 100) or by enzymatic cleavage. Cells employed in expression of antibody and polypeptide can be disrupted by various physical or chemical means, such as freeze-thaw cycling, sonication, mechanical disruption, or cell lysing agents.

It may be desired to purify antibody and polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the antibody and polypeptide. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular antibody or polypeptide produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

I. Pharmaceutical Formulations

Therapeutic formulations of the antibodies, binding oligopeptides, binding organic or inorganic small molecules and/or polypeptides used in accordance with the present invention are prepared for storage by mixing the antibody, polypeptide, oligopeptide or organic/inorganic small molecule having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). The antibody preferably comprises the antibody at a concentration of between 5-200 mg/ml, preferably between 10-100 mg/ml.

The formulations herein may also contain more than one active compound as necessary for the particular indication being treated, preferably those with complementary activities that do not adversely affect each other. For example, in addition to an antibody, binding oligopeptide, or binding organic or inorganic small molecule, it may be desirable to include in the one formulation, an additional antibody, e.g., a second antibody which binds a different epitope on the same polypeptide, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences*, 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

J. Treatment with Antibodies, Binding Oligopeptides and Binding Organic/Inorganic Small Molecules To determine polypeptide (prostasin and/or HAI-1/1B) expression in the cancer, various detection assays are available. In one embodiment, polypeptide overexpression may be analyzed by immunohistochemistry (IHC). Parrafin embedded tissue sections from a tumor biopsy may be subjected to the IHC assay and accorded a polypeptide staining intensity criteria as follows:

Score 0—no staining is observed or membrane staining is observed in less than 10% of tumor cells.

Score 1+—a faint/barely perceptible membrane staining is detected in more than 10% of the tumor cells. The cells are only stained in part of their membrane.

Score 2+—a weak to moderate complete membrane staining is observed in more than 10% of the tumor cells.

Score 3+—a moderate to strong complete membrane staining is observed in more than 10% of the tumor cells.

Those tumors with 0 or 1+ scores for polypeptide expression may be characterized as not overexpressing the polypeptide, whereas those tumors with 2+ or 3+ scores may be characterized as overexpressing the polypeptide.

Alternatively, or additionally, FISH assays such as the INFORM® (sold by Ventana, Ariz.) or PATHVISION® (Vysis, Ill.) may be carried out on formalin-fixed, paraffin-embedded tumor tissue to determine the extent (if any) of polypeptide overexpression in the tumor.

Polypeptide overexpression or amplification may be evaluated using an in vivo detection assay, e.g., by administering a molecule (such as an antibody, oligopeptide or organic small molecule) which binds the molecule to be detected and is tagged with a detectable label (e.g., a radioactive isotope or a fluorescent label) and externally scanning the patient for localization of the label.

As described above, the antibodies, oligopeptides and organic small molecules of the invention have various non-therapeutic applications. The antibodies, oligopeptides and organic/inorganic small molecules of the present invention can be useful for staging of polypeptide-expressing cancers (e.g., in radioimaging). The antibodies, oligopeptides and organic small molecules are also useful for purification or immunoprecipitation of polypeptide from cells, for detection and quantitation of polypeptide in vitro, e.g., in an ELISA or a Western blot, to kill and eliminate polypeptide-expressing cells from a population of mixed cells as a step in the purification of other cells.

Currently, depending on the stage of the cancer, cancer treatment involves one or a combination of the following therapies: surgery to remove the cancerous tissue, radiation therapy, and chemotherapy. Antibody, oligopeptide or organic small molecule therapy may be especially desirable in elderly patients who do not tolerate the toxicity and side effects of chemotherapy well and in metastatic disease where radiation therapy has limited usefulness. The tumor targeting antibodies, oligopeptides and organic/inorganic small molecules of the invention are useful to alleviate polypeptide-expressing cancers upon initial diagnosis of the disease or during relapse. For therapeutic applications, the antibody, oligopeptide or organic/inorganic small molecule can be used alone, or in combination therapy with, e.g., hormones, anti-angiogens, or radiolabelled compounds, or with surgery, cryotherapy, and/or radiotherapy. Antibody, oligopeptide or organic/inorganic small molecule treatment can be administered in conjunction with other forms of conventional therapy, either consecutively with, pre- or post-conventional therapy. Chemotherapeutic drugs such as TAXOTERE® (docetaxel), TAXOL® (palictaxel), estramustine and mitoxantrone are used in treating cancer, in particular, in good risk patients. In the present method of the invention for treating or alleviating cancer, the cancer patient can be administered antibody, oligopeptide or organic/inorganic small molecule in conjunction with treatment with the one or more of the preceding chemotherapeutic agents. In particular, combination therapy with palictaxel and modified derivatives (see, e.g., EP0600517) is contemplated. The antibody, oligopeptide or organic/inorganic small molecule will be administered with a therapeutically effective dose of the chemotherapeutic agent. In another embodiment, the antibody, oligopeptide or organic/inorganic small molecule is administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, a conjugate comprising an antibody, oligopeptide or organic/inorganic small molecule conjugated with a cytotoxic agent is administered to the patient. Preferably, the immunoconjugate bound to the protein is internalized by the cell, resulting in increased therapeutic efficacy of the immunoconjugate in killing the cancer cell to which it binds. In one embodiment, the cytotoxic agent targets or interferes with the nucleic acid in the cancer cell. Examples of such cytotoxic agents are described above and include maytansinoids, calicheamicins, ribonucleases and DNA endonucleases.

The antibodies, oligopeptides, organic/inorganic small molecules or toxin conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody, oligopeptide or organic small molecule is preferred.

Other therapeutic regimens may be combined with the administration of the antibody, oligopeptide or organic/inorganic small molecule. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the antibody or antibodies, oligopeptides or organic/inorganic small molecules, with administration of an antibody directed against another tumor antigen associated with the particular cancer.

In another embodiment, the therapeutic treatment methods of the present invention involves the combined administration of an antibody (or antibodies), oligopeptides or organic/inorganic small molecules and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody, oligopeptide or organic/inorganic small molecule may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the antibody, oligopeptide or organic/inorganic small molecule (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody, oligopeptide or organic/inorganic small molecule therapy. Suitable dosages for any of the above co-administered agents are those presently used and may be lowered due to the combined action (synergy) of the agent and antibody, oligopeptide or organic/inorganic small molecule.

For the prevention or treatment of disease, the dosage and mode of administration will be chosen by the physician according to known criteria. The appropriate dosage of antibody, oligopeptide or organic/inorganic small molecule will depend on the type of disease to be treated, as defined above, the severity and course of the disease, whether the antibody, oligopeptide or organic/inorganic small molecule is administered for preventive or therapeutic purposes, previous therapy, the patient's clinical history and response to the antibody, oligopeptide or organic/inorganic small molecule, and the discretion of the attending physician. The antibody, oligopeptide or organic/inorganic small molecule is suitably administered to the patient at one time or over a series of treatments. Preferably, the antibody, oligopeptide or organic/inorganic small molecule is administered by intravenous infusion or by subcutaneous injections. Depending on the type and severity of the disease, about 1 µg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the antibody. However, other dosage regimens may be useful. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., *Science* 256:808-813 (1992). See also WO 93/25673 and the references cited therein.

The antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies an antibody sequence is fused to a heterologous polypeptide sequence. The antibodies can be modified in the Fc region to provide desired effector functions. As discussed in more detail in the sections herein, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody competes for binding or bind substantially to, the same epitope as the antibodies of the invention. Antibodies having the biological characteristics of the present antibodies of the invention are also contemplated, specifically including the in vivo tumor targeting and any cell proliferation inhibition or cytotoxic characteristics.

Methods of producing the above antibodies are described in detail herein.

The present antibodies, oligopeptides and organic/inorganic small molecules are useful for treating a prostasin-associated cancer, or alleviating one or more symptoms of the cancer in a mammal. Methods of the invention encompass usage of antagonists in the treatment and/or alleviation of symptoms of metastatic tumors associated with these cancers. The antibody, oligopeptide or organic/inorganic small molecule antagonist is able to bind to at least a portion of the cancer cells that express the polypeptide(s) (prostasin and/or HAI-1/1B) in the mammal. In one embodiment, the antibody, oligopeptide or organic/inorganic small molecule is effective to destroy or kill polypeptide-expressing and/or -responsive tumor cells or inhibit the growth of such tumor cells, in vitro or in vivo, upon binding to the polypeptide. Such an antibody includes a naked antibody (not conjugated to any agent). Naked antibodies that have cytotoxic or cell growth inhibition properties can be further harnessed with a cytotoxic agent to render them even more potent in tumor cell destruction. Cytotoxic properties can be conferred to an antibody by, e.g., conjugating the antibody with a cytotoxic agent, to form an immunoconjugate as described herein. In some embodiments, the cytotoxic agent or a growth inhibitory agent is a small molecule. In some embodiments, toxins such as calicheamicin or a maytansinoid and analogs or derivatives thereof, are used.

The invention provides a composition comprising an antibody, oligopeptide or organic/inorganic small molecule of the invention, and a carrier. For the purposes of treating cancer, compositions can be administered to the patient in need of such treatment, wherein the composition can comprise one or more antibodies present as an immunoconjugate or as the naked antibody. In a further embodiment, the compositions can comprise these antibodies, oligopeptides or organic/inorganic small molecules in combination with other therapeutic agents such as cytotoxic or growth inhibitory agents, including chemotherapeutic agents. The invention also provides formulations comprising an antibody, oligopeptide or organic/inorganic small molecule of the invention, and a carrier. In one embodiment, the formulation is a therapeutic formulation comprising a pharmaceutically acceptable carrier.

Another aspect of the invention is isolated nucleic acids encoding the antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a cancer or alleviating one or more symptoms of the cancer in a mammal, comprising administering a therapeutically effective amount of an antibody, oligopeptide or organic/inorganic small molecule to the mammal. The antibody, oligopeptide or organic/inorganic small molecule therapeutic compositions can be administered short term (acute) or chronic, or intermittent as directed by physician. Also provided are methods of inhibiting the growth of, and killing a polypeptide (prostasin and/or HAI-1/1B)-expressing and/or -responsive cell.

The invention also provides kits and articles of manufacture comprising at least one antibody, oligopeptide or organic/inorganic small molecule. Kits containing antibodies, oligopeptides or organic/inorganic small molecules find use, e.g., for cell killing assays, for purification or immunoprecipitation of polypeptide from cells. For example, for isolation and purification of a polypeptide, the kit can contain an antibody, oligopeptide or organic/inorganic small molecule coupled to beads (e.g., sepharose beads). Kits can be provided which contain the antibodies, oligopeptides or organic/inorganic small molecules for detection and quantitation of a polypeptide in vitro, e.g., in an ELISA or a Western blot. Such antibody, oligopeptide or organic/inorganic small molecule useful for detection may be provided with a label such as a fluorescent or radiolabel.

K. Articles of Manufacture and Kits

Another embodiment of the invention is an article of manufacture containing materials useful for the treatment of a polypeptide (prostasin and/or HAI-1/1B) expressing cancer, such as prostate and ovarian cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the cancer condition and may have a sterile access port (for example the container may be an intravenous solution bag or a vial having a stopper pierceable by a hypodermic injection needle). At least one active agent in the composition is an antibody, oligopeptide or organic/inorganic small molecule of the invention. The label or package insert indicates that the composition is used for treating cancer. The label or package insert will further comprise instructions for administering the antibody, oligopeptide or organic/inorganic small molecule composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for polypeptide-expressing or cell killing assays, for purification or immunoprecipitation of a polypeptide from cells. For isolation and purification of a polypeptide, the kit can contain an antibody, oligopeptide or organic/inorganic small molecule coupled to beads (e.g., sepharose beads). Kits can be provided which contain the antibodies, oligopeptides or organic/inorganic small molecules for detection and quantitation of a polypeptide in vitro, e.g., in an ELISA or a Western blot. As with the article of manufacture, the kit comprises a container and a label or package insert on or associated with the container. The container holds a composition comprising at least one antibody, oligopeptide or organic/inorganic small molecule of the invention. Additional containers may be included that contain, e.g., diluents and buffers, control antibodies. The label or package insert may provide a description of the composition as well as instructions for the intended in vitro or detection use.

L. Polypeptides and Polypeptide-Encoding Nucleic Acids—Specific Forms and Applications Nucleotide sequences (or their complement) encoding polypeptides of the invention have various applications in the art of molecular biology, including uses as hybridization probes, in chromosome and gene mapping and in the generation of anti-sense RNA and DNA probes. Polypeptide-encoding nucleic acid will also be useful for the preparation of polypeptides by the recombinant techniques described herein, wherein those polypeptides may find use, for example, in the preparation of antibodies as described herein.

A full-length native sequence polypeptide gene, or portions thereof, may be used as hybridization probes for a cDNA library to isolate other cDNAs (for instance, those encoding naturally-occurring variants of a polypeptide or a polypeptide from other species) which have a desired sequence identity to a native polypeptide sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence polypeptide. By way of example, a screening method will comprise isolating the coding region of the polypeptide gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the polypeptide gene of the present invention can be used to screen libraries of human cDNA, genomic DNA or mRNA to determine which members of such libraries the probe hybridizes to.

Other useful fragments of the polypeptide-encoding nucleic acids include antisense or sense oligonucleotides comprising a singe-stranded nucleic acid sequence (either RNA or DNA) capable of binding to target a polypeptide mRNA (sense) or a polypeptide DNA (antisense) sequence. Antisense or sense oligonucleotides, according to the present invention, comprise a fragment of the coding region of a DNA encoding prostasin, HAI-1/1B or binding fragments as described herein. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The antisense oligonucleotides thus may be used to block expression of a protein, wherein the protein may play a role in the induction of cancer in mammals. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Preferred intragenic sites for antisense binding include the region incorporating the translation initiation/start codon (5'-AUG/5'-ATG) or termination/stop codon (5'-UAA, 5'-UAG and 5-UGA/5'-TAA, 5'-TAG and 5'-TGA) of the open reading frame (ORF) of the gene. These regions refer to a portion of the mRNA or gene that encompasses from about 25 to about 50 contiguous nucleotides in either direction (i.e., 5' or 3') from a translation initiation or termination codon. Other preferred regions for antisense binding include: introns; exons; intron-exon junctions; the open reading frame (ORF) or "coding region," which is the region between the translation initiation codon and the translation termination codon; the 5' cap of an mRNA which comprises an N7-methylated guanosine residue joined to the 5'-most residue of the mRNA via a 5'-5' triphosphate linkage and includes 5' cap structure itself as well as the first 50 nucleotides adjacent to the cap; the 5' untranslated region (5'UTR), the portion of an mRNA in the 5' direction from the translation initiation codon, and thus including nucleotides between the 5' cap site and the translation initiation codon of an mRNA or corresponding nucleotides on the gene; and the 3' untranslated region (3'UTR), the portion of an mRNA in the 3' direction from the translation termination codon, and thus including nucleotides between the translation termination codon and 3' end of an mRNA or corresponding nucleotides on the gene.

Specific examples of preferred antisense compounds useful for inhibiting expression of a polypeptide include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of phosphorus-containing linkages include, but are not limited to, U.S. Pat. Nos.: 3,687,808; 4,469,863;

4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH.sub.2 component parts. Representative United States patents that teach the preparation of such oligonucleosides include, but are not limited to,. U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred antisense oligonucleotides, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., Science, 1991, 254, 1497-1500.

Preferred antisense oligonucleotides incorporate phosphorothioate backbones and/or heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] described in the above referenced U.S. Pat. No. 5,489,677, and the amide backbones of the above referenced U.S. Pat. No. 5,602,240. Also preferred are antisense oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-alkyl, S-alkyl, or N-alkyl; O-alkenyl, S-alkeynyl, or N-alkenyl; O-alkynyl, S-alkynyl or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred antisense oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'—O—$CH_2CH_2OCH_3$, also known as 2'—O—(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O($CH_2$)$_{2ON(CH3)}$$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'—O—$CH_2$—O—$CH_2$—N($CH_3$)$_2$.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'—O—$CH_3$), 2'-aminopropoxy (2'—O$CH_2CH_2NH_2$); 2'-allyl (2'—$CH_2$—CH=$CH_2$), 2'—O-allyl (2'—O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$ or —$CH_2$—C≡CH) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi et al, Antisense Research and Applications, CRC Press, Boca Raton, 1993, pp. 276-278) and are preferred base substitutions, even more particularly when combined with 2'-O-methoxyethyl sugar modifications. Representative United States patents that teach the preparation of modified nucleobases include, but are not limited to: U.S. Pat. No. 3,687,808, as well as U.S. Pat. Nos.: 4,845,205; 5,130, 302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941 and 5,750,692, each of which is herein incorporated by reference.

Another modification of antisense oligonucleotides chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, cation lipids, phospholipids, cationic phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) and U.S. Pat. Nos.: 4,828, 979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Preferred chimeric antisense oligonucleotides incorporate at least one 2' modified sugar (preferably 2'—O—(CH$_2$)$_2$—O—CH$_3$) at the 3' terminal to confer nuclease resistance and a region with at least 4 contiguous 2'—H sugars to confer RNase H activity. Such compounds have also been referred to in the art as hybrids or gapmers. Preferred gapmers have a region of 2' modified sugars (preferably 2'—O—(CH$_2$)$_2$—O—CH$_3$) at the 3'-terminal and at the 5' terminal separated by at least one region having at least 4 contiguous 2'—H sugars and preferably incorporate phosphorothioate backbone linkages. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521, 291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 nucleotides in length, alternatively at least about 10, 20, 30, 50, 60, 70, 80, 90, 100, 150, 200, 250, 300, 350, 400, 450, 500, 550, 600, 650, 700, 750, 800, 850, 900, 950, or 1000 nucleotides in length, wherein in this context the term "about" means the referenced nucleotide sequence length plus or minus 10% of that referenced length.

The probes may also be employed in PCR techniques to generate a pool of sequences for identification of closely related polypeptide coding sequences.

Nucleotide sequences encoding a polypeptide can also be used to construct hybridization probes for mapping the gene which encodes that polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

The polypeptide can be used in assays to identify other proteins or molecules involved in a binding interaction with the polypeptide. By such methods, inhibitors of the receptor/ ligand binding interaction can be identified. Proteins involved in such binding interactions can also be used to screen for peptide or small molecule inhibitors of the binding interaction. Screening assays can be designed to find lead compounds that mimic the biological activity of a native polypeptide or a receptor for the polypeptide. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode a polypeptide or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a polypeptide can be used to clone genomic DNA encoding the polypeptide in accordance with established techniques and the genomic sequences used to generate transgenic animals that contain cells which express DNA encoding the polypeptide. Methods for generating transgenic animals, particularly animals such as mice or rats, have become conventional in the art and are described, for example, in U.S. Pat. Nos. 4,736,866 and 4,870,009. Typically, particular cells would be targeted for polypeptide transgene incorporation with tissue-specific enhancers. Transgenic animals that include a copy of a transgene encoding a polypeptide introduced into the germ line of the animal at an embryonic stage can be used to examine the effect of increased expression of DNA encoding a polypeptide. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of a polypeptide can be used to construct a gene "knock out" animal which has a defective or altered gene encoding the polypeptide as a result of homologous recombination between the endogenous gene encoding the polypeptide and altered genomic DNA encoding the polypeptide introduced into an embryonic stem cell of the animal. For example, cDNA encoding the polypeptide can be used to clone genomic DNA encoding the polypeptide in accordance with established techniques. A portion of the genomic DNA encoding the polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the polypeptide.

Nucleic acid encoding the polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The nucleic acid molecules encoding the polypeptides or fragments thereof described herein are useful for chromosome identification. In this regard, there exists an ongoing need to identify new chromosome markers, since relatively few chromosome marking reagents, based upon actual sequence data are presently available. Each nucleic acid molecule of the present invention can be used as a chromosome marker.

Polypeptides and nucleic acid molecules of the invention may be used diagnostically for tissue typing, wherein the polypeptides may be differentially expressed in one tissue as compared to another, preferably in a diseased tissue as compared to a normal tissue of the same tissue type. Nucleic acid molecules will find use for generating probes for PCR, Northern analysis, Southern analysis and Western analysis.

This invention encompasses methods of screening compounds to identify those that prevent the effect of the polypeptide (antagonists). Screening assays for antagonist drug candidates are designed to identify compounds that bind or complex with the polypeptides encoded by the genes identified herein, or otherwise interfere with the interaction of the encoded polypeptides with other cellular proteins, including e.g., inhibiting the expression of the polypeptide from cells. Such screening assays will include assays amenable to highthroughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide or the drug candidate is immobilized on a solid phase, e.g., on a microtiter plate, by covalent or non-covalent attachments. Non-covalent attachment generally is accomplished by coating the solid surface with a solution of the polypeptide and drying. Alternatively, an immobilized antibody, e.g., a monoclonal antibody, specific for the polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a polypeptide, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (*London*), 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the polypeptide may be added to a cell along with the compound to be screened for a particular activity and the ability of the compound to inhibit the activity of interest in the presence of the polypeptide indicates that the compound is an antagonist to the polypeptide. Alternatively, antagonists may be detected by combining the polypeptide and a potential antagonist with membrane-bound polypeptide receptors or encoded receptors under appropriate conditions for a competitive inhibition assay. The polypeptide can be labeled, such as by radioactivity, such that the number of polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the polypeptide and a cDNA library created from this RNA is divided into pools and used to transfect COS cells or other cells that are not responsive to the polypeptide. Transfected cells that are grown on glass slides are exposed to labeled polypeptide. The polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled polypeptide can be photoaffinity-linked with cell membrane or extract preparations that express the receptor molecule.

Cross-linked material is resolved by PAGE and exposed to X-ray film. The labeled complex containing the receptor can be excised, resolved into peptide fragments, and subjected to protein micro-sequencing. The amino acid sequence obtained from micro- sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled polypeptide in the presence of the candidate compound. The ability of the compound to enhance or block this interaction could then be measured.

More specific examples of potential antagonists include an oligonucleotide that binds to the fusions of immunoglobulin with a polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the polypeptide that recognizes the receptor but imparts no effect, thereby competitively inhibiting the action of the polypeptide.

Another potential antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides herein, can be used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the polypeptide. The antisense RNA oligonucleotide hybridizes to the mRNA in vivo and blocks translation of the mRNA molecule into the polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the polypeptide, thereby blocking the normal biological activity of the polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Isolated polypeptide-encoding nucleic acid can be used for recombinantly producing polypeptide using techniques well known in the art and as described herein. In turn, the produced polypeptides can be employed for generating antibodies using techniques well known in the art and as described herein.

Antibodies specifically binding a polypeptide identified herein, as well as other molecules identified by the screening assays disclosed hereinbefore, can be administered for the treatment of various disorders, including cancer, in the form of pharmaceutical compositions.

If the polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The following examples are offered for illustrative purposes only, and are not intended to limit the scope of the present invention in any way.

EXAMPLES

Reagents—sHAI-1B and its mutants, sHAI-1B(R260A) and sHAI-1B(K401A), were expressed and purified as previously described (Kirchhofer, Peek et al. 2003). KD1 containing amino acids $Thr^{246}$-$Val^{303}$ of HAI-1B precursor was expressed in *E. coli* and purified as described (Shia, Stamos et al. 2004). Aprotinin-agarose was purchased from Sigma, aprotinin from Roche (Indianapolis, Ind.), chromogenic substrate S2765 from DiaPharma Group, Inc. (West Chester, Ohio), OVCAR3 cell line from ATCC (Manassas, Va.), non-immunized mouse IgG from Jackson ImmunoResearch Laboratories, Inc. (West Grove, Pa.). Alzheimer's amyloid β protein precursor inhibitor (APPI) and KALI-DY (Dennis, Herzka et al. 1995) (Genentech, Inc., South San Francisco, Calif., USA). *Screening for protease inhibitors co-expressed with prostasin*—The Genesis Enterprise System™ database (Gene Logic, Inc., Gaithersburg, Md.) containing gene expression signatures from over 8000 clinical samples from various normal and disease conditions on the Affymetrix HG-U133A and B GeneChip® microarrays was used as a source of gene expression data. From this database, each probe set on the microarray has a gene expression profile consisting of the expression results of each of the samples. The gene expression profile can be considered as a vector of expression values, one value for each sample. We limited our analysis to samples from epithelium-containing tissues labeled in the database as normal, and to those tissues that contained more than 20 normal samples. For each of these tissues, we performed a search starting with the gene expression profile for prostasin (Affymetrix probeset 202525_at), comparing it with the profiles for each of the other probesets. The comparison of a given probeset with that of prostasin can be visualized as a scatterplot, with the expression value of prostasin on the x-axis and the expression value of the given probeset on the y-axis, and each sample from the given tissue represented by a point in the scatterplot. From this scatterplot, the co-expression of the given probeset with prostasin can be measured by the Pearson correlation coefficient r. High values of r indicate probesets with a gene expression profile similar to the starting probeset (Graeber and Eisenberg 2001). We sorted all probesets by their value of r, and then filtered these lists to identify protease inhibitors that had high correlation coefficients. Probesets corresponding to putative protease inhibitors were obtained by searching the NetAffx database (Liu, Loraine et al. 2003) for those annotated as belonging to a Gene Ontology molecular function of protease inhibitor activity (GO identification 0030414) or one of its subtypes (0042031, 0030415, 0004866, 0019828, 0004869, 0030161, 0008191, 0004867, 0030569, 0030568, 0030304) (http://www.godatabase.org/cgi-bin/amigo/go.cgi). This search yielded 177 Affymetrix probesets on the HG-U133A and HG-U133B microarrays.

Reverse Transcription-PCR—Total RNAs from various human tissues were purchased from BD Biosciences Clontech (Palo Alto, Calif.). These total RNAs were processed by use of oligo(dT)24 and SuperScript reverse transcriptase (Invitrogen, Carlsbad, Calif.). The cDNAs were subjected to PCR using the primer set of prostasin, HAI-1/1B or β-actin (as a control). The sequences of these primers were as follows: 5'-CCTGGGGCCTGGGCAGC-3' (SEQ ID NO:3) and 5'-TGCGGCTCCTCAGGCTTGG-3' (SEQ ID NO:4) for prostasin; 5'-ATGGAGGCTGCTTGGGCAACA-3' (SEQ ID NO:5) and 5'-ACAGGCAGCCTCGTCGGAGG-3' (SEQ ID NO:6) for HAI-1/1B; 5'-TCACCCACACTGTGCCCATC-TACGA-3' (SEQ ID NO:7) and 5'-CAGCGGAACCGCT-CATTGCCAATGG-3' (SEQ ID NO:8) for β-actin. The PCR amplifications were carried out for 25 cycles of 45 sec at 95° C., 45 sec at 55° C. (for HAI-1/1B) or 65° C. (for prostasin and 1 min at 72° C. using Advantage-GC cDNA polymerase mix (BD Biosciences Clontech). The reverse transcription-PCR products were separated on a 2.5% agarose gel and then visualized by ethidium bromide staining.

Cloning, expression, and purification of prostasin—Full-length human prostasin was inserted into eukaryotic expression vector pRK5E. Recombinant protein was produced using a transient transfection process in CHO cells. Briefly, the cells were transfected with DNA-cationic lipid complex preformed for 15 min in basal medium, and were then grown in 3-liter spinner flasks in Dulbecco's modified Eagle's medium (DMEM) supplemented with 2 mg/l recombinant human insulin and trace elements. The culture was maintained at 33° C. for 5 days. The conditioned medium was harvested and loaded onto an aprotinin-agarose (Sigma) column equilibrated with 20 mM Tris/Cl, pH7.5. After washing with the same buffer, prostasin was eluted with 100 mM glycine, pH 3.0, containing 150 mM NaCl. The eluates were neutralized by 0.5 M Tris immediately. Pooled prostasin fractions were concentrated and dialyzed against 20 mM Tris-HCl, pH7.5, 150 mM NaCl. N-terminal amino acid sequence analysis gave a sequence of $^{13}$ITGGSSAVAGQW$^{24}$ (SEQ ID NO:9), indicating that purified prostasin was in the active two-chain form. Protein concentration was determined by use of the Bicinchoninic Acid Assay (Pierce, Rockford, Ill.).

Generation of antibodies—To obtain polyclonal antibodies against sHAI-1B or prostasin, 0.3 mg/animal recombinant protein was injected into each rabbit by Antibody Solutions (Palo Alto, Ccalif.). After 9-11 weeks, the rabbit sera with the highest titers were purified by a protein A affinity chromatography. Mouse monoclonal antibody 6E9 against sHAI-1B was generated using standard hybridoma producing techniques (Kohler and Milstein 1975). Hybridoma cell lines secreting antibody specific for sHAI-1B, as determined by ELISA, were cloned twice by limiting dilution and further characterized. The monoclonal antibody was then purified from ascites fluid by protein A affinity chromatography.

Immunoblotting—Proteins were separated on 4-20% SDS-PAGE gels and transferred to nitrocellulose membranes (Invitrogen). After blocking the nonspecific binding sites with 2% BSA in PBS, the membrane was incubated with primary antibody followed by incubation with 1:40,000 dilution of a goat anti-mouse or a donkey anti-rabbit horseradish peroxidase-conjugated secondary antibody (Jackson ImmunoResearch Laboratories, Inc., West Grove, Pa.) and detected by use of the ECL plus system (Amersham Biosciences Inc.). The primary antibodies used were as follows: polyclonal anti-HAI-1B antibody (used at 4 µg/ml), monoclonal anti-HAI-1B antibody (used at 3 µg/ml), monoclonal anti-prostasin antibody (used at 1:500, BD Biosciences).

Prostasin binding assay—Purified prostasin and sHAI-1B were diluted in 20 mM Tris-Cl, pH 9.0 containing 0.01% Triton X-100 (TT buffer) to the final concentration as indicated. The mixture was incubated at 37° C. for 0.5 h or 2 h and the reaction was stopped by addition of SDS sample buffer with DTT. Some of the samples were boiled for 5 min as indicated in the figures. 30 µl of each sample was analyzed by immunoblotting.

Enzyme inhibition assay—Inhibitors were incubated with prostasin (final concentration, 3 nM) in 225 µl TT buffer for 20 min at room temperature before addition of 25 µl of 0.5 mM S2765 (final concentration, 0.05 mM; $K_m$, 0.05 mM). The increase in absorbance at 405 nm was monitored on a kinetic microplate reader (Molecular Devices, Sunnyvale, Calif.). The linear rates of the increase in absorbance were expressed as percentage activities ($100\% \times v_i/v_0$). Inhibitor activity was calculated as the concentration of inhibitor giving 50% inhibition ($IC_{50}$) of the uninhibited enzyme activity. At least three independent experiments were performed for each inhibitor.

Transfection of CHO cell lines with plasmid DNA encoding full-length HAI-1B—Full-length HAI-1B was cloned by PCR as described previously (Kirchhofer, Peek et al. 2003) and inserted into the expression vector pRK5E. HAI-1B or vector alone was transferred into CHO cells using FuGENE 6 transfection reagent (Roche) according to the manufacturer's protocol. HAI-1B and vector stably transfected CHO cell lines were designated CHO/HAI-1B and CHO/vector, respectively.

HAI-1B ectodomain shedding assay—CHO/HAI-1B and CHO/vector cells were grown to 50% confluence in DMEM plus 10% serum in 6-well plates. Cells were washed with PBS and grown to 90% confluence in serum-free medium supplemented with 2 mg/l recombinant human insulin and trace elements. Then 1 ml of fresh serum-free medium with or without 200 ng/ml prostasin was added. After continued incubation for 2 h or 24 h, 300 µl medium was collected and centrifuged at 5,000 rpm for 5 min on a desktop microtube centrifuge. The supernatant was mixed with SDS-, DTT-containing sample buffer and then concentrated by a Microcon® centrifugal filter device (YM-10) (Millipore, Billerica, Mass.) to 30 µl. Samples were boiled and analyzed by immunoblotting. To harvest cell lysates, cells were washed with PBS and incubated with 300 µl M-PER™ lysis buffer (Pierce) per well for 5 min at room temperature. Then the cell lysates were centrifuged at 14,000×g for 30 min at 4° C. 10 µl supernatant was used for immunoblot analysis.

Isolation and detection of the prostasin:HAI-1/1B complexesfrom cell culture—Antibodies were immobilized to Aminolink® Plus Coupling Gel (Pierce) according to manufacturer's protocol. The coupling efficiency was determined by measuring protein concentration of the starting material and non-bound fraction. The amount of coupled antibody ranged from 1.4 mg/ml to 2.3 mg/ml resin. CHO/HAI-1B and CHO/vector cells were grown as described for the HAI-1B ectodomain shedding assay, except that they were grown in 10 cm dishes. When cells reached 90% confluence, 3 ml of fresh serum-free medium with or without 200 ng/ml prostasin was added. After 2 h, the medium was harvested and centrifuged at 5,000×g to remove cell debris. To co-immunoprecipitate the complexes from the cell membrane, the cells were washed and lysed with 1 ml M-PER™ lysis buffer and centrifuged at 14,000×g for 30 min at 4° C. 3 ml medium or 900 µl cell lysate was mixed with the antibody-coupled resin (containing 100 µg antibody) and incubated at 4° C. with end-to-end rotation overnight. The resin was then washed with PBS and the bound proteins eluted with 60 µl ImmunoPure® IgG elution buffer (Pierce). For isolation of the complexes from the medium of OVCAR3 cells, cells were grown to 90% confluence in 250 ml DMEM plus 10% serum in a 2-liter roller bottle. The medium was collected and loaded onto a Poly-Prep column (Bio-Rad Laboratories) prepacked with the antibody-coupled resin (containing 350 µg antibody) at room temperature. The resin was then washed with PBS and the bound proteins eluted with 500 µl ImmunoPure® IgG elution buffer. SDS sample buffer with DTT was added to the eluates and boiled for 5 min before each sample was analyzed by immunoblotting.

Results

Similar expression profiles of prostasin and HAI-1/1B—A co-expression search was conducted to find prostasin inhibitors on the assumption that natural inhibitors may have similar gene expression patterns as their target enzymes. The 177 probesets used represented 111 different inhibitors of all major protease inhibitor families. Data analysis revealed HAI-1 (represented by Affymetrix probeset 202826_at) as a high ranking protease inhibitor in normal tissues (Table I). HAI-1 ranked highest in 7 and second highest in 6 of the 17 examined tissues. The p-values for these tissues were all statistically significant (P<0.005). In cases where HAI-1 was not the highest-ranking protease inhibitor, the table shows the protease inhibitor that did rank highest. In three cases where HAI-1 ranked second (cervix, endometrium, and esophagus), the highest-ranking protease inhibitor was hepatocyte growth factor activator inhibitor-2 (HAI-2), a bi-Kunitz type serine protease inhibitor structurally related to HAI-1.

TABLE I

Ranking of HAI-1 in co-expression analysis of prostasin

| Organ | Nsample[c] | HAI-1 (202826_at) | | Highest ranking PI[d] | |
|---|---|---|---|---|---|
| | | r[b] | p-value | rank[c] | (probeset, r[b]) |
| Breast | 86 | 0.547 | 1.09e−07 | 2 | PCSKIN (218952_at, 0.579) |
| Cervix | 112 | 0.725 | 4.21e−19 | 2 | HAI-2 (210715_s_at, 0.746) |
| Colorectal | 323 | 0.822 | 7.35e−80 | 1 | |
| Endometrium | 27 | 0.755 | 6.78e−06 | 2 | HAI-2 (210715_s_at, 0.746) |
| Esophagus | 28 | 0.715 | 2.51e−05 | 2 | HAI-2 (210715_s_at, 0.774) |
| Kidney | 101 | 0.429 | 1.52e−05 | 5 | Amyloid beta (208702_x_at, 0.475) |
| Lung | 142 | 0.505 | 3.86e−10 | 2 | SPINK4 (207214_at, 0.581) |
| Ovary | 159 | 0.803 | 1.22e−36 | 1 | |
| Pancreas | 49 | −0.029 | 0.389 | 94 | PBP (210825_s_at, 0.530) |
| Placenta | 23 | 0.592 | 0.00342 | 1 | |
| Prostate | 62 | 0.650 | 2.12e−08 | 2 | PCSKIN (218952_at, 0.669) |
| Skin | 70 | 0.722 | 3.65e−12 | 1 | |
| Small intestine | 189 | 0.834 | 1.12e−49 | 1 | |
| Stomach | 72 | 0.797 | 1.13e−16 | 1 | |
| Testis | 22 | 0.274 | 0.174 | 48 | DEFB126 (221414_s_at, 0.960) |
| Thymus | 69 | 0.292 | 0.0192 | 8 | TFPI2 (209278_s_at, 0.366) |
| Thyroid | 28 | 0.630 | 4.29e−04 | 1 | |

[a]Nsample, number of samples in the database;
[b]r, Pearson correlation coefficient;
[c]rank, the ranking of HAI-1 among protease inhibitors;
[d]PI, protease inhibitor which ranked highest in cases where HAI-1 was not the highest-ranking inhibitor;
PCSKIN, proprotein convertase subtilisin/kexin type 1 inhibitor (GenBank: BC002851);
HAI-2, hepatocyte growth factor activator inhibitor type-2 (GenBank: AB006534);
Amyloid beta (GenBank: AF168956);
SPINK4, serine protease inhibitor, Kazal type 4 (GenBank: AF048700);
PBP, prostatic binging protein (GenBank: BC008714);
DEFB126, beta-defensin 126 (GenBank: AF525928);
TFPI2, tissue factor pathway inhibitor 2 (GenBank: AF217542).

The Affymetrix probeset for HAI-1 were from the 3′ UTR and, therefore, the expression data reflected the combined expression of both splice variants HAI-1 and HAI-1B. In order to determine whether prostasin expression correlates with both or either of the isoforms, the expression of prostasin, HAI-1 and HAI-1B in 21 tissues were examined by reverse transcription-PCR (FIG. 1). The results showed that in all tissues with high prostasin expression—lung, placenta, prostate, salivary gland, thyroid gland, trachea, colon and small intestine—both HAI-1 isoforms were highly expressed as well. These findings are in full agreement with the Affymetrix microarray data showing that HAI-1/1B ranked as the highest or second highest protease inhibitor in these prostasin-abundant tissues.

Prostasin and sHAI-1B form 1:1 complexes—Soluble prostasin was purified from conditioned medium of CHO cells transiently transfected with full-length prostasin. N-terminal sequencing and SDS-PAGE analysis of purified prostasin indicated that activation cleavage at $Arg^{12}$-$Ile^{13}$ had occurred, yielding the enzymatically active two-chain form. Prostasin was incubated with sHAI-1B comprising the entire extracellular domain of HAI-1B (Kirchhofer, Peek et al. 2003) at different molar ratios (FIG. 2A). Increasing concentrations of prostasin shifted the sHAI-1B band (55 kDa) to the higher molecular mass species of 85 kDa, indicating the formation of prostasin:sHAI-1B complexes. At a 10-fold molar excess of prostasin, almost all sHAI-1B was bound to prostasin. Immunoblotting with anti-prostasin antibody confirmed that the 85 kDa band comprised complexes of sHAI-1B and prostasin (data not shown). Heat denaturation of the complex produced the expected sHAI-1B band (58 kDa) indicating that prostasin, even at molar excess, does not degrade sHAI-1B. The apparent molecular mass of 85 kDa indicated that prostasin and sHAI-1B formed a 1:1 complex. We did not detect any higher molecular mass complexes, suggesting that only one of the two sHAI-1B Kunitz domains did engage in prostasin binding. To identify the Kunitz domain interacting with prostasin, we utilized two sHAI-1B mutants in which the Kunitz domains were separately inactivated by changing the $P_1$ residues $Arg^{260}$ (in KD1) and $Lys^{401}$ (in KD2) to Ala (Kirchhofer, Peek et al. 2003). As shown in FIG. 2B, the KD2 mutant sHAI-1B(K401A) still formed an 85 kDa complex with prostasin, whereas the KD1 mutant sHAI-1B(R260A) did not. These results suggested that sHAI-1B binds to prostasin through KD1.

Prostasin activity is inhibited by sHAI-1B—In screening a panel of synthetic para-nitroanilide substrates, we identified N-α-Z-D-Arg-Gly-Arg-pNA-2HCl (S2765) as the most suitable prostasin substrate and it was used for subsequent inhibition assays. Wildtype sHAI-1B inhibited the amidolytic activity of prostasin towards S2765 with an $IC_{50}$ value of 66±15.2 nM (Table II). In agreement with the binding data, sHAI-1B(R260A) was at least 18-fold less potent ($IC_{50}$ >1000 nM), whereas sHAI-1B(K401A) showed inhibitory potency comparable to the wildtype. Furthermore, the 60-amino acid KD1 ($Thr^{246}$-$Val^{303}$) potently inhibited prostasin enzymatic activity with an $IC_{50}$ of 4.7±0.5 nM. Other Kunitz domains, such as Alzheimer's amyloid βprotein precursor (APPI) and KALI-DY (Dennis, Herzka et al. 1995) did not inhibit prostasin (Table II). Aprotinin inhibited prostasin with an $IC_{50}$ of 1.2±0.1 nM, which is comparable to the value obtained by Yu et al. (Yu, Chao et al. 1994) using prostasin purified from human seminal fluid.

TABLE II

Effects of inhibitors on the activity of prostasin

| Inhibitors | $IC_{50}$ (nM) |
|---|---|
| sHAI-1B wt | 66.0 ± 15.2 |
| sHAI-1B K401A | 75.3 ± 12.4 |
| sHAI-1B R260A | >1000 |
| KD1 | 4.7 ± 0.5 |
| sHAI-1 | 109.0 ± 9.2 |
| APPI | >1000 |
| KALI-DY | >1000 |

The $IC_{50}$ values are the averages ± S.D. of at least three independent experiments.

Interaction of prostasin with HAI-1B in cell culture—To determine whether HAI-1B binds to prostasin under more physiologic conditions, we examined whether endogenous prostasin:HAI-1/1B complexes are formed in cell culture. RNA expression experiments showed that the ovarian carcinoma cell line OVCAR3 expressed prostasin as well as both HAI-1 isoforms (FIG. 3A). Expression of the proteins was confirmed by immunoblotting experiments using OVCAR3 cell lysate (data not shown). In the immunoblotting experiments, a 64-kDa band was detected by a polyclonal anti-HAI-1B antibody, which probably represented both isoforms, because the calculated molecular masses of HAI-1 and HAI-1B only differed by 1.5 kDa (data not shown). Immunoaffinity purification of conditioned medium with 6E9, a monoclonal antibody raised against HAI-1B, yielded two major HAI-1/1B fragments, a 58 kDa and a 40 kDa. Probing the blot with an anti-prostasin antibody identified a 38 kDa prostasin band (FIG. 3B), demonstrating that HAI-1/1B and prostasin spontaneously formed endogenous complexes. The antibody 6E9 was found immuno-reactive with both SHAI-1B and sHAI-1 (obtained from R & D Systems, Inc., Minneapolis, Minn.) (data not shown) and, therefore, the two fragments observed could be derived from either or both isoforms.

To further understand the interaction of prostasin with HAI-1B, a stable CHO cell line over-expressing full-length HAI-1B was established. We found that surface-expressed HAI-1B (65 kDa) was spontaneously cleaved releasing identical amounts of the two major HAI-1B fragments into the medium (FIG. 4A). The molecular mass of these fragments, 58 kDa and 40 kDa, were identical to those found in OVCAR3 cell medium (FIG. 3B). No HAI-1B was detected in the CHO/vector cells (FIG. 4A). Both shed HAI-1B fragments were detected as early as 2 h and further incubation resulted in more HAI-1B shedding without changes in the ratio of the two species. To determine whether prostasin formed complexes with shed HAI-1B, the CHO/HAI-1B cells were incubated with prostasin for 2 h and we found prostasin co-immunoprecipitated with the shed HAI-1B (FIG. 4B). The addition of prostasin slightly induced HAI-1B shedding (2-3 fold induction, data not shown) without changing the relative amounts of the 58 kDa and 40 kDa HAI-1B fragments (FIG. 4B, upper panel). Because both the 58 kDa and 40 kDa forms were released into the medium, the question arose as to which molecular species was engaged in complex formation. To answer this question, a similar experiment was performed using the anti-prostasin antibody to co-immunoprecipitate bound HAI-1B fragment. Both the 58 kDa and 40 kDa forms were detected on immunoblots (FIG. 4C), with the 40 kDa form consistently giving the stronger signal compared to the 58 kDa form. This indicated that both HAI-1B fragments are capable of binding prostasin.

Moreover, to demonstrate that prostasin is able to directly interact with HAI-1B on the cell surface, CHO/HAI-1B cells were incubated with prostasin and the formed complexes co-immunoprecipitated from cell lysate with an anti-HAI-1B antibody. The results showed that prostasin specifically binds to membrane HAI-1B (FIG. 4D). To further confirm their interaction on the cell surface, full-length prostasin and HAI-1B were co-expressed in CHO cells. First, transient transfection of CHO/vector and CHO/HAI-1B cells with full-length prostasin resulted in similar levels of membrane-expressed prostasin protein. Second, by using the anti-HAI-1B antibody 6E9, prostasin HAI-1B complexes were immunoprecipitated from the cell membrane fraction and were detected as shed forms in the culture medium (data not shown).

Discussion

In this study we used a bioinformatics approach comparing gene expression profiles of prostasin with genes encoding protease inhibitors to identify physiologic regulators of prostasin. The highest scoring protease inhibitor found was the bi-Kunitz inhibitor HAI-1/1B. RT-PCR experiments further demonstrated that prostasin expression correlated with the expression of both isoforms, HAI-1 and HAI-1B. Like prostasin, HAI-1/1B is specifically expressed on the epithelial cell surface, from where it can be released as a soluble form. HAI-1/1B is known to inhibit several chymotrypsin-like serine proteases, including the epithelial type II transmembrane serine protease (TTSP) matriptase (Lin, Anders et al. 1999). There is strong experimental evidence that matriptase and HAI-1/1B constitute a physiologic enzyme-inhibitor pair, including the isolation of matriptase:HAI-1 complexes from human breast milk (Lin, Anders et al. 1999). Therefore, we expected HAI-1/1B to appear as a matching protease inhibitor for matriptase in a co-expression analysis similar to that carried out for prostasin. Indeed, we found HAI-1/1B as the highest-ranking protease inhibitor in 7 tissues and as second highest in 2 tissues (data not shown), thus corroborating the validity of our bioinformatics approach. The prostasin:HAI-1/1B pair had a similar overall score, HAI-1/1B ranking highest in 7 tissues and second highest in 6 tissues. Consistent with these findings, a co-expression search starting with the HAI-1 probeset 202826_at revealed that prostasin and matriptase ranked as the highest and second highest serine proteases, respectively (data not shown).

Biochemical evidence supporting the proposal that HAI-1/1B and prostasin constitute an inhibitor-enzyme pair was derived from binding and inhibition studies using purified proteins and cellular assays. First, we showed that sHAI-1B formed a stable 1:1 complex with prostasin, indicating that only one of the two sHAI-1B Kunitz domains participated in prostasin binding. By use of two sHAI-1B mutants in which the functions of KD1 and KD2 were separately inactivated by $P_1$-directed mutagenesis, we were able to determine that KD1 accounted for essentially all of the binding activity. Results from prostasin enzymatic assays were entirely consistent with this conclusion, demonstrating that the inhibitory activity of KD2 was <6% of KD1. Therefore, the interaction of prostasin with HAI-1B via KD1 follows the same paradigm known for other target enzymes of HAI-1/1B, such as HGFA, matriptase, trypsin, and plasmin (Denda, Shimomura et al. 2002; Kirchhofer, Peek et al. 2003). It is unclear why KD2, which has 47% sequence identity with KD1, largely lacks binding affinity to these proteases. It is conceivable that an unusual Glu at residue 402 in KD2 instead of a much smaller Gly or Ala found in KD1 and other Kunitz domain inhibitors might cause a steric conflict with its target enzymes, resulting in poor inhibitory activity (Shia, Stamos et al. 2004). Furthermore, recombinant KD1 alone ($Thr^{246}$-$Val^{303}$) was a significantly more potent prostasin inhibitor than sHAI-1B, which is in keeping with the 3—30-fold greater potency of recombinant KD1 for other proteases (Shia, Stamos et al. 2004). This could mean that the protease interaction of KD1 is under allosteric influences by other HAI-1/1B domains, perhaps by the region located C-terminal to KD1 comprising the LDL receptor-like and KD2 domains. Some support for this hypothesis comes from the observation that the shed 40 kDa fragment of HAI-1, which spans the N-terminal region ending with KD1, has greater binding affinity towards HGFA as compared to the 58 kDa fragment containing the additional LDL receptor-like and KD2 domains (Shimomura, Denda et al. 1999).

Studies with HAI-1/1B-expressing cell lines provided further evidence that prostasin and HAI-1/1B interact in-vivo. We found that similar to HGFA and matriptase (Lin, Anders et al. 1999; Kataoka, Shimomura et al. 2000; Benaud, Dickson et al. 2001), prostasin bound to HAI-1B on the cell surface as well as to shed HAI-1/1B fragments. The experiments with OVCAR3 cells, which endogenously express prostasin and both HAI-1 isoforms, demonstrated that complexes of prostasin and HAI-1/1B were present in the conditioned medium. Because co-localization on the cell surface increases reactant concentrations and the probability to form enzyme/inhibitor complexes, we consider it likely that the complexes were initially formed on the cell surface before being shed into the medium. OVCAR3 cells released two major HAI-1/1B forms of 40 kDa and a 58 kDa, which are identical in mass to the HAI-1B fragments identified in the conditioned medium of the MKN45 and HLC-1 cancer cell lines (Shimomura, Denda et al. 1999). Based on N-terminal sequences and binding studies, Shimomura et al. (Shimomura, Denda et al. 1999) showed that the 40 kDa form is an N-terminal fragment containing KD1 while the 58 kDa form comprises most of the extracellular domain including both Kunitz domains. Both forms were detected at about equal concentration in the conditioned medium of CHO cells overexpressing HAI-1B, allowing us to address the question of whether prostasin forms complexes with either of both fragments. Results from immunoprecipitation experiments not only demonstrated that prostasin formed complexes with both the 40 kDa and the 58 kDa form, but further suggested that prostasin preferentially bound to the 40 kDa fragment or formed a more stable complex with the 40 kDa fragment. This interpretation is in keeping with the greater binding affinity of the 40 kDa form to HGFA (Kataoka, Shimomura et al. 2000; Denda, Shimomura et al. 2002) and its ability to form stable complexes with matriptase in human breast milk (Lin, Wang et al. 1997; Benaud, Dickson et al. 2001).

So far there is no experimental evidence suggesting functional differences between the HAI-1 and HAI-1B isoforms. In this regard, it is interesting to note that the 58 kDa fragment was the major shed form of COS-7 cells transfected with full-length HAI-1, whereas very little 40 kDa was detected (Denda, Shimomura et al. 2002). In contrast, our experiments with HAI-1B transfected CHO cells showed that similar amounts of 40 kDa and 58 kDa forms were shed into the medium. The most simple explanation is that the proteolytic processes involved in surface shedding are specific for a given epithelial cell type and/or species, resulting in different shedding profiles for HAI-i and HAI-1B. Nevertheless, it is conceivable that the isoforms undergo different surface processing determined by the presence or absence of the hydrophilic 16-amino acid insert in HAI-1B and HAI-1, respectively. The cleavage site of the 40 kDa form is located near this peptide insert and, therefore, cleavage site recognition by cell surface proteases may be enhanced in the presence of the 16-amino acid insert. This question has particular significance because target enzymes of HAI-1/1B seem to preferentially form complexes with the 40 kDa fragment.

Recently, Chen et al. (Chen, Skinner et al. 2001; Chen, Zhang et al. 2004) identified the PN-1, a member of the serpin family, as a prostasin inhibitor and suggested that PN-1 regulates prostasin activity in prostate epithelium. Because HAI-1/1B co-localizes with prostasin to the prostate glandular epithelium (Yu, Chao et al. 1994; Yu, Chao et al. 1995; Kataoka, Suganuma et al. 1999), it is possible that prostasin enzymatic function in prostate is under the control of several inhibitory systems including PN-1 and HAI-1/1B. In addition, the epithelial bi-Kunitz inhibitor HAI-2 (Marlor, Delaria et al. 1997) was found to potently inhibit prostasin activity in a purified enzyme system (Shipway, Danahay et al. 2004). Interestingly, in our co-expression search (Table I) HAI-2 was identified as the highest-ranking protease inhibitor in the three tissues where HAI-1 ranked second. HAI-2 is expressed in many epithelial tissues and inhibits a broad spectrum of serine proteases in-vitro (Kawaguchi, Qin et al. 1997; Marlor, Delaria et al. 1997).

In conclusion, by use of a bioinformatics co-expression analysis we have identified prostasin and HAI-1B as a physiologic enzyme—inhibitor pair. Supporting evidence came from purified and cellular systems, demonstrating the ability of HAI-1B to form inhibitory complexes with prostasin on the cell surface and in the extracellular environment. Other target enzymes of HAI-1B, such as HGFA and matriptase are implicated in tumor progression (Parr and Jiang 2001; Oberst, Johnson et al. 2002), possibly involving activation of their respective macromolecular substrates, such as pro-HGF and single chain urokinase plasminogen activator (u-PA) (Lee, Dickson et al. 2000; Kataoka, Miyata et al. 2003). The precise mechanism underlying prostasin's function in tumor progression would benefit from further investigation. However, differential regulation of its expression in cancers such as ovarian cancer and high-grade prostate cancer, coupled with the discovery described herein of its inhibition by its physiological inhibitor provides a useful avenue for therapeutic intervention. Furthermore, the purified KD1 derived from HAI-1/1B potently inhibited prostasin and, thus, could itself serve as a useful agent to modulate prostasin enzymatic activity in pathological conditions such as tumor progression and metastasis.

PARTIAL LIST OF REFERENCES

Adachi, M., K. Kitamura, et al. (2001). "Activation of epithelial sodium channels by prostasin in *Xenopus* oocytes." *J Am Soc Nephrol* 12(6): 1114-21.

Benaud, C., R. B. Dickson, et al. (2001). "Regulation of the activity of matriptase on epithelial cell surfaces by a blood-derived factor." *Eur J Biochem* 268(5): 1439-47.

Bouton, M. C., B. Richard, et al. (2003). "The serpin protease-nexin 1 is present in rat aortic smooth muscle cells and is upregulated in L-NAME hypertensive rats." *Arterioscler Thromb Vasc Biol* 23(1): 142-7.

Chen, L. M. and K. X. Chai (2002). "Prostasin serine protease inhibits breast cancer invasiveness and is transcriptionally regulated by promoter DNA methylation." *Int J Cancer* 97(3): 323-9.

Chen, L. M., G. B. Hodge, et al. (2001). "Down-regulation of prostasin serine protease: a potential invasion suppressor in prostate cancer." *Prostate* 48(2): 93-103.

Chen, L. M., M. L. Skinner, et al. (2001). "Prostasin is a glycosylphosphatidylinositol-anchored active serine protease." *J Biol Chem* 276(24): 21434-42.

Chen, L. M., X. Zhang, et al. (2004). "Regulation of prostasin expression and function in the prostate." *Prostate* 59(1): 1-12.

Denda, K., T. Shimomura, et al. (2002). "Functional characterization of Kunitz domains in hepatocyte growth factor activator inhibitor type 1." *J Biol Chem* 277(16): 14053-9.

Dennis, M. S., A. Herzka, et al. (1995). "Potent and selective Kunitz domain inhibitors of plasma kallikrein designed by phage display." *J Biol Chem* 270(43): 25411-7.

Donaldson, S. H., A. Hirsh, et al. (2002). "Regulation of the epithelial sodium channel by serine proteases in human airways." *J Biol Chem* 277(10): 8338-45.

Graeber, T. G. and D. Eisenberg (2001). "Bioinformatic identification of potential autocrine signaling loops in cancers from gene expression profiles." *Nat Genet* 29(3): 295-300.

Itoh, H., H. Kataoka, et al. (2000). "Upregulation of HGF activator inhibitor type 1 but not type 2 along with regeneration of intestinal mucosa." *Am J Physiol Gastrointest Liver Physiol* 278(4): G635-43.

Itoh, H., M. Yamauchi, et al. (2000). "Genomic structure and chromosomal localization of the human hepatocyte growth factor activator inhibitor type 1 and 2 genes." *Eur J Biochem* 267(11): 3351-9.

Kataoka, H., R. Hamasuna, et al. (2000). "Activation of hepatocyte growth factor/scatter factor in colorectal carcinoma." *Cancer Res* 60(21): 6148-59.

Kataoka, H., S. Miyata, et al. (2003). "Roles of hepatocyte growth factor (HGF) activator and HGF activator inhibitor in the pericellular activation of HGF/scatter factor." *Cancer Metastasis Rev* 22(2-3): 223-36.

Kataoka, H., T. Shimomura, et al. (2000). "Hepatocyte growth factor activator inhibitor type 1 is a specific cell surface binding protein of hepatocyte growth factor activator (HGFA) and regulates HGFA activity in the pericellular microenvironment." *J Biol Chem* 275(51): 40453-62.

Kataoka, H., T. Suganuma, et al. (1999). "Distribution of hepatocyte growth factor activator inhibitor type 1 (HAI-1) in human tissues. Cellular surface localization of HAI-1 in simple columnar epithelium and its modulated expression in injured and regenerative tissues." *J Histochem Cytochem* 47(5): 673-82.

Kataoka, H., H. Uchino, et al. (1998). "Evaluation of hepatocyte growth factor activator inhibitor expression in normal and malignant colonic mucosa." *Cancer Lett* 128(2): 219-27.

Kawaguchi, T., L. Qin, et al. (1997). "Purification and cloning of hepatocyte growth factor activator inhibitor type 2, a Kunitz-type serine protease inhibitor." *J Biol Chem* 272(44): 27558-64.

Kirchhofer, D., M. Peek, et al. (2003). "Tissue expression, protease specificity, and Kunitz domain functions of hepatocyte growth factor activator inhibitor-1B (HAI-1B), a new splice variant of HAI-1." *J Biol Chem* 278(38): 36341-9.

Kohler, G. and C. Milstein (1975). "Continuous cultures of fused cells secreting antibody of predefined specificity." *Nature* 256(5517): 495-7.

Lee, S. L., R. B. Dickson, et al. (2000). "Activation of hepatocyte growth factor and urokinase/plasminogen activator by matriptase, an epithelial membrane serine protease." *J Biol Chem* 275(47): 36720-5.

Lin, C. Y., J. Anders, et al. (1999). "Purification and characterization of a complex containing matriptase and a Kunitz-type serine protease inhibitor from human milk." *J Biol Chem* 274(26): 18237-42.

Lin, C. Y., J. K. Wang, et al. (1997). "Characterization of a novel, membrane-bound, 80-kDa matrix-degrading protease from human breast cancer cells. Monoclonal antibody production, isolation, and localization." *J Biol Chem* 272(14): 9147-52.

Liu, G., A. E. Loraine, et al. (2003). "NetAffx: Affymetrix probesets and annotations." *Nucleic Acids Res* 31(1): 82-6.

Marlor, C. W., K. A. Delaria, et al. (1997). "Identification and cloning of human placental bikunin, a novel serine protease inhibitor containing two Kunitz domains." *J Biol Chem* 272(18): 12202-8.

Mok, S. C., J. Chao, et al. (2001). "Prostasin, a potential serum marker for ovarian cancer: identification through microarray technology." *J Natl Cancer Inst* 93(19): 1458-64.

Muthukumar, T., R. Ding, et al. (2003). "Serine proteinase inhibitor-9, an endogenous blocker of granzyme B/perforin lytic pathway, is hyperexpressed during acute rejection of renal allografts." *Transplantation* 75(9): 1565-70.

Oberst, M. D., M. D. Johnson, et al. (2002). "Expression of the serine protease matriptase and its inhibitor HAI-1 in epithelial ovarian cancer: correlation with clinical outcome and tumor clinicopathological parameters." *Clin Cancer Res* 8(4): 1101-7.

Parr, C. and W. G. Jiang (2001). "Expression of hepatocyte growth factor/scatter factor, its activator, inhibitors and the c-Met receptor in human cancer cells." *Int J Oncol* 19(4): 857-63.

Phillips, T., J. T. Opferman, et al. (2004). "A role for the granzyme B inhibitor serine protease inhibitor 6 in CD8+ memory cell homeostasis." *J Immunol* 173(6): 3801-9.

Richard, B., V. Arocas, et al. (2004). "Protease nexin-1: a cellular serpin down-regulated by thrombin in rat aortic smooth muscle cells." *J Cell Physiol* 201(1): 138-45.

Shia, S., J. L. Stamos, et al. (2004). "Induced fit in the active site of serine proteases: structures of Hepatocyte Growth Factor Activator (HGFA) alone and with the inhibitory domain from HGFA Inhibitor-1B." *J. Molecular Biology* in press.

Shimomura, T., K. Denda, et al. (1999). "Multiple sites of proteolytic cleavage to release soluble forms of hepatocyte growth factor activator inhibitor type 1 from a transmembrane form." *J Biochem (Tokyo)* 126(5): 821-8.

Shimomura, T., K. Denda, et al. (1997). "Hepatocyte growth factor activator inhibitor, a novel Kunitz-type serine protease inhibitor." *J Biol Chem* 272(10): 6370-6.

Shipway, A., H. Danahay, et al. (2004). "Biochemical characterization of prostasin, a channel activating protease." *Biochem Biophys Res Commun* 324(2): 953-63.

Takahashi, S., S. Suzuki, et al. (2003). "Down-regulated expression of prostasin in high-grade or hormone-refractory human prostate cancers." *Prostate* 54(3): 187-93.

Tong, Z., B. Illek, et al. (2004). "Prostasin, a membrane-anchored serine peptidase, regulates sodium currents in JME/CF15 cells, a cystic fibrosis airway epithelial cell line." Am *J Physiol Lung Cell Mol Physiol.*

Tyagi, S. C., S. G. Kumar, et al. (1995). "Co-expression of tissue inhibitor and matrix metalloproteinase in myocardium." *J Mol Cell Cardiol* 27(10): 2177-89.

Yu, J. X., L. Chao, et al. (1994). "Prostasin is a novel human serine proteinase from seminal fluid. Purification, tissue distribution, and localization in prostate gland." *J Biol Chem* 269(29): 18843-8.

Yu, J. X., L. Chao, et al. (1995). "Molecular cloning, tissue-specific expression, and cellular localization of human prostasin mRNA." *J Biol Chem* 270(22): 13483-9.

The invention claimed is:

1. A method of screening for a candidate inhibitor substance that inhibits HAI-1/1B inhibition of prostasin, said method comprising: (a) contacting a candidate substance with a first sample comprising prostasin, HAI-1/1B, and a prostasin substrate, and (b) comparing amount of prostasin activity in the sample with amount of prostasin activity in a control sample that has not been contacted with said candidate substance, whereby an increase in amount of prostasin activity in the first sample compared to the control sample indicates that the candidate substance is capable of inhibiting HAI-1/1B inhibition of prostasin.

2. A method of screening for a candidate inhibitor substance that blocks specific binding between prostasin and HAI-1/1B, said method comprising (a) contacting a candidate substance with purified prostasin andlor purified HAI-1/1B, and (b) detecting binding, if any, to the prostasin and or HAI-1/1B.

3. The method of claim 1 or 2, wherein the substance competes with HAI-1/HAI-1B, for binding to prostasin, wherein the substance does not substantially inhibit prostasin activity.

4. The method of claim 1 or 2, wherein the substance competes with a KD1 domain of HAI-1/HAI-1B for binding to prostasin, wherein the substance does not substantially inhibit prostasin activity.

5. The method of claim 1 or 2, wherein the substance competes with prostasin for binding to HAI-1/HAI-1B.

6. The method of claim 1 or 2, wherein the method comprises determining whether prostasin and HAI-1/HAI-1B form a complex.

7. The method of claim 1 or 2, wherein the method comprises determining whether prostasin and a KD domain of HAI-1/HAI-1B form a complex.

8. The method of claim 1 or 2, wherein the first sample comprises prostasin, HAI-1, and a prostasin substrate.

9. The method of claim 1 or 2, wherein the first sample comprises prostasin, HAI-1B, and a prostasin substrate.

10. The method of claim 3 or 5, wherein the first sample comprises prostasin, HAI-1, and a prostasin substrate.

11. The method of claim 3 or 5, wherein the first sample comprises prostasin, HAI-1B, and a prostasin substrate.

* * * * *

UNITED STATES PATENT AND TRADEMARK OFFICE
CERTIFICATE OF CORRECTION

PATENT NO. : 7,622,265 B2 Page 1 of 1
APPLICATION NO. : 11/359865
DATED : November 24, 2009
INVENTOR(S) : Fan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 656 days.

Signed and Sealed this

Twenty-sixth Day of October, 2010

David J. Kappos
*Director of the United States Patent and Trademark Office*

```
                       SEQUENCE LISTING

<160> NUMBER OF SEQ ID NOS: 9

<210> SEQ ID NO 1
<211> LENGTH: 343
<212> TYPE: PRT
<213> ORGANISM: Homo sapiens

<400> SEQUENCE: 1

Met Ala Gln Lys Gly Val Leu Gly Pro Gly Gln Leu Gly Ala Val
 1               5                   10                  15

Ala Ile Leu Leu Tyr Leu Gly Leu Leu Arg Ser Gly Thr Gly Ala
                20                  25                  30

Glu Gly Ala Glu Ala Pro Cys Gly Val Ala Pro Gln Ala Arg Ile
                35                  40                  45

Thr Gly Gly Ser Ser Ala Val Ala Gly Gln Trp Pro Trp Gln Val
                50                  55                  60

Ser Ile Thr Tyr Glu Gly Val His Val Cys Gly Gly Ser Leu Val
                65                  70                  75

Ser Glu Gln Trp Val Leu Ser Ala Ala His Cys Phe Pro Ser Glu
                80                  85                  90

His His Lys Glu Ala Tyr Glu Val Lys Leu Gly Ala His Gln Leu
                95                  100                 105

Asp Ser Tyr Ser Glu Asp Ala Lys Val Ser Thr Leu Lys Asp Ile
                110                 115                 120

Ile Pro His Pro Ser Tyr Leu Gln Glu Gly Ser Gln Gly Asp Ile
                125                 130                 135

Ala Leu Leu Gln Leu Ser Arg Pro Ile Thr Phe Ser Arg Tyr Ile
                140                 145                 150

Arg Pro Ile Cys Leu Pro Ala Ala Asn Ala Ser Phe Pro Asn Gly
                155                 160                 165

Leu His Cys Thr Val Thr Gly Trp Gly His Val Ala Pro Ser Val
                170                 175                 180

Ser Leu Leu Thr Pro Lys Pro Leu Gln Gln Leu Glu Val Pro Leu
                185                 190                 195

Ile Ser Arg Glu Thr Cys Asn Cys Leu Tyr Asn Ile Asp Ala Lys
                200                 205                 210

Pro Glu Glu Pro His Phe Val Gln Glu Asp Met Val Cys Ala Gly
                215                 220                 225
```

```
Tyr Val Glu Gly Gly Lys Asp Ala Cys Gln Gly Asp Ser Gly Gly
                230                 235                 240

Pro Leu Ser Cys Pro Val Glu Gly Leu Trp Tyr Leu Thr Gly Ile
            245                 250                 255

Val Ser Trp Gly Asp Ala Cys Gly Ala Arg Asn Arg Pro Gly Val
        260                 265                 270

Tyr Thr Leu Ala Ser Ser Tyr Ala Ser Trp Ile Gln Ser Lys Val
    275                 280                 285

Thr Glu Leu Gln Pro Arg Val Val Pro Gln Thr Gln Glu Ser Gln
            290                 295                 300

Pro Asp Ser Asn Leu Cys Gly Ser His Leu Ala Phe Ser Ser Ala
        305                 310                 315

Pro Ala Gln Gly Leu Leu Arg Pro Ile Leu Phe Leu Pro Leu Gly
    320                 325                 330

Leu Ala Leu Gly Leu Leu Ser Pro Trp Leu Ser Glu His
            335                 340

<210> SEQ ID NO 2
<211> LENGTH: 58
<212> TYPE: PRT
<213> ORGANISM: Homo sapiens

<400> SEQUENCE: 2

Thr Glu Asp Tyr Cys Leu Ala Ser Asn Lys Val Gly Arg Cys Arg
  1               5                  10                  15

Gly Ser Phe Pro Arg Trp Tyr Tyr Asp Pro Thr Glu Gln Ile Cys
             20                  25                  30

Lys Ser Phe Val Tyr Gly Gly Cys Leu Gly Asn Lys Asn Asn Tyr
         35                  40                  45

Leu Arg Glu Glu Glu Cys Ile Leu Ala Cys Arg Gly Val
             50                  55

<210> SEQ ID NO 3
<211> LENGTH: 17
<212> TYPE: DNA
<213> ORGANISM: Artificial sequence
<220> FEATURE:
<223> OTHER INFORMATION: sequence is synthesized
<220> FEATURE:
<221> NAME/KEY: Primer
<222> LOCATION: full
<223> OTHER INFORMATION: Synthesized

<400> SEQUENCE: 3
cctggggcct gggcagc                                                17

<210> SEQ ID NO 4
<211> LENGTH: 19
<212> TYPE: DNA
<213> ORGANISM: Artificial sequence
<220> FEATURE:
<223> OTHER INFORMATION: sequence is synthesized
<220> FEATURE:
<221> NAME/KEY: Primer
<222> LOCATION: full
<223> OTHER INFORMATION: Synthesized

<400> SEQUENCE: 4
tgcggctcct caggcttgg                                              19

<210> SEQ ID NO 5
<211> LENGTH: 21
```

-continued

```
<212> TYPE: DNA
<213> ORGANISM: Artificial sequence
<220> FEATURE:
<223> OTHER INFORMATION: sequence is synthesized
<220> FEATURE:
<221> NAME/KEY: Primer
<222> LOCATION: full
<223> OTHER INFORMATION: Synthesized

<400> SEQUENCE: 5
atggaggctg cttgggcaac  a                                              21

<210> SEQ ID NO 6
<211> LENGTH: 20
<212> TYPE: DNA
<213> ORGANISM: Artificial sequence
<220> FEATURE:
<223> OTHER INFORMATION: sequence is synthesized
<220> FEATURE:
<221> NAME/KEY: Primer
<222> LOCATION: full
<223> OTHER INFORMATION: Synthesized

<400> SEQUENCE: 6
acaggcagcc tcgtcggagg                                                 20

<210> SEQ ID NO 7
<211> LENGTH: 25
<212> TYPE: DNA
<213> ORGANISM: Artificial sequence
<220> FEATURE:
<223> OTHER INFORMATION: sequence is synthesized
<220> FEATURE:
<221> NAME/KEY: Primer
<222> LOCATION: full
<223> OTHER INFORMATION: Synthesized

<400> SEQUENCE: 7
tcacccacac tgtgcccatc  tacga                                          25

<210> SEQ ID NO 8
<211> LENGTH: 25
<212> TYPE: DNA
<213> ORGANISM: Artificial sequence
<220> FEATURE:
<223> OTHER INFORMATION: sequence is synthesized
<220> FEATURE:
<221> NAME/KEY: Primer
<222> LOCATION: full
<223> OTHER INFORMATION: Synthesized

<400> SEQUENCE: 8
cagcggaacc gctcattgcc  aatgg                                          25

<210> SEQ ID NO 9
<211> LENGTH: 12
<212> TYPE: PRT
<213> ORGANISM: Homo sapiens

<400> SEQUENCE: 9

Ile Thr Gly Gly Ser Ser Ala Val Ala Gly Gln Trp
                5                  10
```